United States Patent [19]
Storkus et al.

[11] Patent Number: 5,989,565
[45] Date of Patent: Nov. 23, 1999

[54] ELUTION AND IDENTIFICATION OF T CELL EPITOPES FROM VIABLE CELLS

[75] Inventors: Walter J. Storkus, Glenshaw; Michael T. Lotze, Pittsburgh, both of Pa.

[73] Assignee: University of Pittsburgh, Pittsburgh, Pa.

[21] Appl. No.: 08/474,120

[22] Filed: Jun. 7, 1995

Related U.S. Application Data

[63] Continuation-in-part of application No. 08/011,007, Jan. 29, 1993, abandoned.
[51] Int. Cl.$^6$ .......................... A61K 34/00; A61K 39/00; C07K 5/00; C12P 21/02
[52] U.S. Cl. .......................... 424/277.1; 514/21; 530/344; 435/70.1
[58] Field of Search .......................... 530/344; 424/277.1; 514/21; 435/70.1

[56] References Cited

PUBLICATIONS

Rotzschke et al Nature (Nov. 15, 1990) vol. 348, pp. 252–254.
Storkus et al J of Immunol vol 151, 3719–3727, Oct. 1, 1993.
Kawakami et al Proc. Natl. Acad. Sci. vol. 91, 3515–3519, Apr. 1994.
Anchini et al J. Immunol vol. 142, 3692–3701 May 15, 1989.
Zinkernagel, R.M., et al., *Adv, Immunol.* 27:51 (1979).
Doherty, P.C., et al., *Adv. Cancer Res.* 42:1 (1984).
Zinkernagel, R.M., et al., *Nature* 248:701 (1974).
Townsend, A., et al., *Cell* 42:457 (1985).
Townsend, A., et al., *Cell* 44:959 (1986).
Yewdell, J.W., et al., *Scince* 244:1072 (1989).
Townsend, A., et al., *Cell* 62:285 (1990).
Nuchtern, J.G., et al., *Nature* 339:223 (1989).
Rotzschke, O., et al., *Nature* 348:252 (1990).
Van Bleek, G.M., et al., *Nature* 348:213 (1990).
Rotzschke, O., et al., *Science* 249:283 (1990).
Falk, K., et al., *Nature* 348:248 (1990).
Jardetsky, T.S., et al., *Nature* 351:326 (1991).
Falk, K., et al., *Nature* 351:290 (1991).
Nikolic–Zugic, J., et al., *Immunol, Rev.* 10:54 (1991).
Kornstein, M.J., et al., *Cancer Res.* 43:2749 (1983).
Van Duinen, S.G., et al., *Cancer Res.* 48:1019 (1988).
Lotze, M.T., *Pigment Cell* 10:163 (1990).

Rosenberg, S.A., et al., *N. Eng. J. Med.* 319:1676 (1988).
Parmiani, G., et al., *J. Natl. Cancer Inst.* 82:361 (1990).
Van den Eynde, B., et al., *Int. J. Cancer* 44:634 (1984).
Anichini, A., et al., *J. Immunol.* 142: 3692 (1989).
Wolfel, T., et al., *Eur. J. Immunol.* 24:759 (1994).
Crowley, N.J., et al., *J. Immunol.* 146:1692 (1991).
Traversari, C., et al., *J. Exp. Med.* 176:1453 (1991).
Kawakani, Y., et al., *J. Exp. Med.* 180:347 (1994).
Hom, S.S., et al., *J. Immunother.* 10:153 (1991).
McMichael, A.J., et al., *Eur. J. Immunol.* 8:705 (1978).
Suguwara, S., et al., *J. Immunol Meth.* 100:83 (1987).
Gillet, A.C., et al., *Eur. J. Immunol.* 20:759 (1990).
Biddison, W.E., et al., *J. Immunol.* 129:730 (1982).
Mitchell, M.S., et al., *J. Clin. Oncol.* 10:1158 (1992).
Gorga, J.C., et al., *Crit Rev. Immunol.* 11:305 (1992).
Storkus, W.J., et al., *Proc. Nat. Acad. Sci. USA* 88:5989 (1991).
Storkus, W.J., et al., *Proc. Nat. Acad. Sci. USA* 86:2361 (1989).
Carbone, F.R., et al., *J. Exp. Med.* 167:1767(1988).
Kawakami, Y., et al., *J. Immunol.* 148:638 (1992).
Storkus, W.J., et al., *J. Immunol.* 143:3853 (1989).
Wolfel, T., et al., *Immunogenet.* 26:178 (1987).
Anichini, A., et al., *J. Exp. Med.* 177:989 (1993).
Whiteside, T.L., et al., *J. Immunol. Methods* 90:221 (1981).
McMichael, A.J., et al., *Hum. Immunol.* 1:121 (1980).
Zeh, H.J., et al., *Hum. Immunol* 39:79 (1994).
Salter, R.D., et al., *Immunogenetics* 21:235 (1985).
Cox, A.L., et al., *Science (Wash., DC)* 264:716 (1994).
Culmann, B.E., et al., *Eur. J. Immunol.* 19:2383 (1989).
Kawakami, Y., et al., *Proc. Nat. Acad Sci USA* 91:3515.
Nijman, H.W., et al., *Eur. J. Immunol.* 23:1215 (1993).
Boyd, L.F., et al., *Proc. Nat. Acad Sci USA* 89:2242 (1992).
Bodmer, H.G., et al., *Nature (Land.)* 342:443 (1989).

*Primary Examiner*—Lila Feisee
*Assistant Examiner*—Geetha P. Bansal
*Attorney, Agent, or Firm*—Reed Smith Shaw & McClay LLP

[57] ABSTRACT

Methods are provided for eluting peptides that are bound to major histocompatibility complex ("MHC") molecules expressed on the cell surfaces of viable cells that have at least one MHC-peptide complex on the surfaces of the cells, the method comprising incubating the cells in the presence of peptide elution buffer, preferably comprising iso-osmotic, citrate-phosphate buffer at a pH of approximately 3.3, for between about 15 seconds and one minute. Using these methods a naturally processed melanoma peptide recognized by CD8$^+$ cytotoxic T lymphocytes has been identified.

7 Claims, 13 Drawing Sheets

```
                           SEQUENCE LISTING (1) GENERAL INFORMATION:

(iii) NUMBER OF SEQUENCES:  42

(2) INFORMATION FOR SEQ ID NO: 1:

(i) SEQUENCE CHARACTERISTICS:
        (A) LENGTH:12 amino acids
        (B) TYPE:amino acid
        (D) TOPOLOGY:linear (ii) MOLECULE TYPE:peptide (iii) HYPOTHETICAL:no (ix) FEATURE:
        (A) NAME/KEY:Flu M1 57-68
        (D) OTHER INFORMATION:synthetic peptide (xi) SEQUENCE DESCRIPTION:  SEQ ID NO: 1:

Lys Gly Ile Leu Gly Phe Val Phe Thr Leu Thr Val
 1               5                  10

(2) INFORMATION FOR SEQ ID NO: 2:

(i) SEQUENCE CHARACTERISTICS:
        (A) LENGTH:  9 amino acids
        (B) TYPE:amino acid
        (C) TOPOLOGY:linear (ii) MOLECULE TYPE:peptide (iii) HYPOTHETICAL:yes (ix) FEATURE:
        (A) NAME/KEY:Flu M1 58-66
        (B) OTHER INFORMATION:  synthetic peptide (xi) SEQUENCE DESCRIPTION:SEQ ID NO: 2:

Gly Ile Ile Gly Phe Val Phe Thr Ile
 1               5

(2) INFORMATION FOR SEQ ID NO:3:
```

(i) SEQUENCE CHARACTERISTICS:
        (A) LENGTH: 9 amino acids
        (B) TYPE:amino acid
        (C) TOPOLOGY:linear (ii) MOLECULE TYPE:peptide (iii) HYPOTHETICAL:yes (ix) FEATURE:
        (A) NAME/KEY:Flu M1 58-66
        (B) OTHER INFORMATION: synthetic peptide (xi) SEQUENCE DESCRIPTION:SEQ ID NO: 3:

Gly Ile Ile Gly Phe Val Phe Thr Leu
 1               5

(2) INFORMATION FOR SEQ ID NO:4:

(i) SEQUENCE CHARACTERISTICS:
        (A) LENGTH: 9 amino acids
        (B) TYPE:amino acid
        (C) TOPOLOGY:linear (ii) MOLECULE TYPE:peptide (iii) HYPOTHETICAL:yes (ix) FEATURE:
        (A) NAME/KEY:Flu M1 58-66
        (B) OTHER INFORMATION: synthetic peptide (xi) SEQUENCE DESCRIPTION:SEQ ID NO: 4:

Gly Ile Leu Gly Phe Val Phe Thr Leu
 1               5

(2) INFORMATION FOR SEQ ID NO:5:

(i) SEQUENCE CHARACTERISTICS:
        (A) LENGTH: 9 amino acids
        (B) TYPE:amino acid
        (C) TOPOLOGY:linear (ii) MOLECULE TYPE:peptide (iii) HYPOTHETICAL:yes (ix) FEATURE:
        (A) NAME/KEY:Flu M1 58-66
        (B) OTHER INFORMATION: synthetic peptide (xi) SEQUENCE DESCRIPTION:SEQ ID NO: 5:

Gly Leu Leu Gly Phe Val Phe Thr Leu
 1               5

(2) INFORMATION FOR SEQ ID NO:6:

(i) SEQUENCE CHARACTERISTICS:
        (A) LENGTH:9 amino acids
        (B) TYPE:amino acid
        (D) TOPOLOGY:linear (ii) MOLECULE TYPE:peptide (iii) HYPOTHETICAL:yes (ix) FEATURE:
        (A) NAME/KEY:p939
        (D) OTHER INFORMATION:synthetic peptide (xi) SEQUENCE DESCRIPTION: SEQ ID NO: 6:

Ile Ile Thr Val Ile Ile Gly Val Ile
 1               5

```
(2) INFORMATION FOR SEQ ID NO:7:

(i) SEQUENCE CHARACTERISTICS:
        (A) LENGTH:  9 amino acids
        (B) TYPE:amino acid
        (C) TOPOLOGY:linear (ii) MOLECULE TYPE:peptide (iii) HYPOTHETICAL:yes (ix) FEATURE:
        (A) NAME/KEY:p939
        (B) OTHER INFORMATION:  synthetic peptide (xi) SEQUENCE DESCRIPTION:SEQ ID NO: 7:

Ile Leu Thr Val Ile Ile Gly Val Ile
 1               5

(2) INFORMATION FOR SEQ ID NO:8:

(i) SEQUENCE CHARACTERISTICS:
        (A) LENGTH:  9 amino acids
        (B) TYPE:amino acid
        (C) TOPOLOGY:linear (ii) MOLECULE TYPE:peptide (iii) HYPOTHETICAL:yes (ix) FEATURE:
        (A) NAME/KEY:p939
        (B) OTHER INFORMATION:  synthetic peptide (xi) SEQUENCE DESCRIPTION:SEQ ID NO: 8:

Ile Ile Thr Val Leu Ile Gly Val Ile
 1               5

(2) INFORMATION FOR SEQ ID NO:9:

(i) SEQUENCE CHARACTERISTICS:
        (A) LENGTH:  9 amino acids
        (B) TYPE:amino acid
        (C) TOPOLOGY:linear (ii) MOLECULE TYPE:peptide (iii) HYPOTHETICAL:yes (ix) FEATURE:
        (A) NAME/KEY:p939
        (B) OTHER INFORMATION:  synthetic peptide (xi) SEQUENCE DESCRIPTION:SEQ ID NO: 9:

Ile Ile Thr Val Ile Leu Gly Val Ile
 1               5

(2) INFORMATION FOR SEQ ID NO:10:

(i) SEQUENCE CHARACTERISTICS:
        (A) LENGTH:  9 amino acids
        (B) TYPE:amino acid
        (C) TOPOLOGY:linear (ii) MOLECULE TYPE:peptide (iii) HYPOTHETICAL:yes (ix) FEATURE:
        (A) NAME/KEY:p939
        (B) OTHER INFORMATION:  synthetic peptide
```

(xi) SEQUENCE DESCRIPTION:SEQ ID NO: 10:

Ile Ile Thr Val Ile Ile Gly Val Leu
 1               5

(2) INFORMATION FOR SEQ ID NO:11:

(i) SEQUENCE CHARACTERISTICS:
        (A) LENGTH:9 amino acids
        (B) TYPE:amino acid
        (D) TOPOLOGY:linear (ii) MOLECULE TYPE:peptide (iii) HYPOTHETICAL:yes (ix) FEATURE:
        (A) NAME/KEY:p939
        (D) OTHER INFORMATION:synthetic peptide (xi) SEQUENCE DESCRIPTION:  SEQ ID NO: 11:

Leu Ile Thr Val Ile Ile Gly Val Ile
 1               5

(2) INFORMATION FOR SEQ ID NO:12:

(i) SEQUENCE CHARACTERISTICS:
        (A) LENGTH:  9 amino acids
        (B) TYPE:amino acid
        (C) TOPOLOGY:linear (ii) MOLECULE TYPE:peptide (iii) HYPOTHETICAL:yes (ix) FEATURE:
        (A) NAME/KEY:p939
        (B) OTHER INFORMATION:  synthetic peptide (xi) SEQUENCE DESCRIPTION:SEQ ID NO: 12:

Leu Leu Thr Val Ile Ile Gly Val Ile
 1               5

(2) INFORMATION FOR SEQ ID NO:13:

(i) SEQUENCE CHARACTERISTICS:
        (A) LENGTH:  9 amino acids
        (B) TYPE:amino acid
        (C) TOPOLOGY:linear (ii) MOLECULE TYPE:peptide (iii) HYPOTHETICAL:yes (ix) FEATURE:
        (A) NAME/KEY:p939
        (B) OTHER INFORMATION:  synthetic peptide (xi) SEQUENCE DESCRIPTION:SEQ ID NO: 13:

Leu Ile Thr Val Leu Ile Gly Val Ile
 1               5

(2) INFORMATION FOR SEQ ID NO:14:

(i) SEQUENCE CHARACTERISTICS:
        (A) LENGTH:  9 amino acids
        (B) TYPE:amino acid
        (C) TOPOLOGY:linear (ii) MOLECULE TYPE:peptide (iii) HYPOTHETICAL:yes

```
        (ix) FEATURE:
              (A) NAME/KEY:p939
              (B) OTHER INFORMATION:   synthetic peptide (xi) SEQUENCE DESCRIPTION:SEQ ID NO: 14:

Leu Ile Thr Val Ile Leu Gly Val Ile
 1                   5

(2) INFORMATION FOR SEQ ID NO:15:

(i) SEQUENCE CHARACTERISTICS:
              (A) LENGTH:  9 amino acids
              (B) TYPE:amino acid
              (C) TOPOLOGY:linear (ii) MOLECULE TYPE:peptide (iii) HYPOTHETICAL:yes (ix) FEATURE:
              (A) NAME/KEY:p939
              (B) OTHER INFORMATION:   synthetic peptide (xi) SEQUENCE DESCRIPTION:SEQ ID NO: 15:

Leu Ile Thr Val Ile Ile Gly Val Leu
 1                   5

(2) INFORMATION FOR SEQ ID NO:16:

(i) SEQUENCE CHARACTERISTICS:
              (A) LENGTH:9 amino acids
              (B) TYPE:amino acid
              (D) TOPOLOGY:linear (ii) MOLECULE TYPE:peptide (iii) HYPOTHETICAL:yes (ix) FEATURE:
              (A) NAME/KEY:p939
              (D) OTHER INFORMATION:synthetic peptide (xi) SEQUENCE DESCRIPTION:   SEQ ID NO: 16:

Ile Leu Thr Val Leu Ile Gly Val Ile
 1                   5

(2) INFORMATION FOR SEQ ID NO:17:

(i) SEQUENCE CHARACTERISTICS:
              (A) LENGTH:  9 amino acids
              (B) TYPE:amino acid
              (C) TOPOLOGY:linear (ii) MOLECULE TYPE:peptide (iii) HYPOTHETICAL:yes (ix) FEATURE:
              (A) NAME/KEY:p939
              (B) OTHER INFORMATION:   synthetic peptide (xi) SEQUENCE DESCRIPTION:SEQ ID NO: 17:

Ile Leu Thr Val Ile Leu Gly Val Ile
 1                   5

(2) INFORMATION FOR SEQ ID NO:18:

(i) SEQUENCE CHARACTERISTICS:
              (A) LENGTH:  9 amino acids
              (B) TYPE:amino acid
              (C) TOPOLOGY:linear
```

(ii) MOLECULE TYPE:peptide (iii) HYPOTHETICAL:yes (ix) FEATURE:
            (A) NAME/KEY:p939
            (B) OTHER INFORMATION:  synthetic peptide (xi) SEQUENCE DESCRIPTION:SEQ ID NO: 18:

Ile Leu Thr Val Ile Ile Gly Val Leu
 1               5

(2) INFORMATION FOR SEQ ID NO:19:

(i) SEQUENCE CHARACTERISTICS:
            (A) LENGTH:  9 amino acids
            (B) TYPE:amino acid
            (C) TOPOLOGY:linear (ii) MOLECULE TYPE:peptide (iii) HYPOTHETICAL:yes (ix) FEATURE:
            (A) NAME/KEY:p939
            (B) OTHER INFORMATION:  synthetic peptide (xi) SEQUENCE DESCRIPTION:SEQ ID NO: 19:

Ile Ile Thr Val Leu Leu Gly Val Ile
 1               5

(2) INFORMATION FOR SEQ ID NO:20:

(i) SEQUENCE CHARACTERISTICS:
            (A) LENGTH:  9 amino acids
            (B) TYPE:amino acid
            (C) TOPOLOGY:linear (ii) MOLECULE TYPE:peptide (iii) HYPOTHETICAL:yes (ix) FEATURE:
            (A) NAME/KEY:p939
            (B) OTHER INFORMATION:  synthetic peptide (xi) SEQUENCE DESCRIPTION:SEQ ID NO: 20:

Ile Ile Thr Val Leu Ile Gly Val Leu
 1               5

(2) INFORMATION FOR SEQ ID NO:21:

(i) SEQUENCE CHARACTERISTICS:
            (A) LENGTH:9 amino acids
            (B) TYPE:amino acid
            (D) TOPOLOGY:linear (ii) MOLECULE TYPE:peptide (iii) HYPOTHETICAL:yes (ix) FEATURE:
            (A) NAME/KEY:p939
            (D) OTHER INFORMATION:synthetic peptide (xi) SEQUENCE DESCRIPTION:  SEQ ID NO: 21:

Ile Ile Thr Val Ile Leu Gly Val Leu
 1               5

(2) INFORMATION FOR SEQ ID NO:22:

(i) SEQUENCE CHARACTERISTICS:

```
          (A) LENGTH:  9 amino acids
          (B) TYPE:amino acid
          (C) TOPOLOGY:linear (ii) MOLECULE TYPE:peptide (iii) HYPOTHETICAL:yes (ix) FEATURE:
          (A) NAME/KEY:p939
          (B) OTHER INFORMATION:  synthetic peptide (xi) SEQUENCE DESCRIPTION:SEQ ID NO: 22:

Leu Leu Thr Val Leu Ile Gly Val Ile
  1               5

(2) INFORMATION FOR SEQ ID NO:23:

(i) SEQUENCE CHARACTERISTICS:
          (A) LENGTH:  9 amino acids
          (B) TYPE:amino acid
          (C) TOPOLOGY:linear (ii) MOLECULE TYPE:peptide (iii) HYPOTHETICAL:yes (ix) FEATURE:
          (A) NAME/KEY:p939
          (B) OTHER INFORMATION:  synthetic peptide (xi) SEQUENCE DESCRIPTION:SEQ ID NO: 23:

Leu Leu Thr Val Ile Leu Gly Val Ile
  1               5

(2) INFORMATION FOR SEQ ID NO:24:

(i) SEQUENCE CHARACTERISTICS:
          (A) LENGTH:  9 amino acids
          (B) TYPE:amino acid
          (C) TOPOLOGY:linear (ii) MOLECULE TYPE:peptide (iii) HYPOTHETICAL:yes (ix) FEATURE:
          (A) NAME/KEY:p939
          (B) OTHER INFORMATION:  synthetic peptide (xi) SEQUENCE DESCRIPTION:SEQ ID NO: 24:

Leu Leu Thr Val Ile Ile Gly Val Leu
  1               5

(2) INFORMATION FOR SEQ ID NO:25:

(i) SEQUENCE CHARACTERISTICS:
          (A) LENGTH:  9 amino acids
          (B) TYPE:amino acid
          (C) TOPOLOGY:linear (ii) MOLECULE TYPE:peptide (iii) HYPOTHETICAL:yes (ix) FEATURE:
          (A) NAME/KEY:p939
          (B) OTHER INFORMATION:  synthetic peptide (xi) SEQUENCE DESCRIPTION:SEQ ID NO: 25:

Ile Leu Thr Val Leu Leu Gly Val Ile
  1               5
```

(2) INFORMATION FOR SEQ ID NO:26:

(i) SEQUENCE CHARACTERISTICS:
        (A) LENGTH:9 amino acids
        (B) TYPE:amino acid
        (D) TOPOLOGY:linear (ii) MOLECULE TYPE:peptide (iii) HYPOTHETICAL:yes (ix) FEATURE:
        (A) NAME/KEY:p939
        (D) OTHER INFORMATION:synthetic peptide (xi) SEQUENCE DESCRIPTION: SEQ ID NO: 26:

Ile Leu Thr Val Leu Ile Gly Val Leu
 1          5

(2) INFORMATION FOR SEQ ID NO:27:

(i) SEQUENCE CHARACTERISTICS:
        (A) LENGTH:  9 amino acids
        (B) TYPE:amino acid
        (C) TOPOLOGY:linear (ii) MOLECULE TYPE:peptide (iii) HYPOTHETICAL:yes (ix) FEATURE:
        (A) NAME/KEY:p939
        (B) OTHER INFORMATION:  synthetic peptide (xi) SEQUENCE DESCRIPTION:SEQ ID NO: 27:

Ile Ile Thr Val Leu Leu Gly Val Leu
 1          5

(2) INFORMATION FOR SEQ ID NO:28:

(i) SEQUENCE CHARACTERISTICS:
        (A) LENGTH:  9 amino acids
        (B) TYPE:amino acid
        (C) TOPOLOGY:linear (ii) MOLECULE TYPE:peptide (iii) HYPOTHETICAL:yes (ix) FEATURE:
        (A) NAME/KEY:p939
        (B) OTHER INFORMATION:  synthetic peptide (xi) SEQUENCE DESCRIPTION:SEQ ID NO: 28:

Leu Ile Thr Val Leu Leu Gly Val Ile
 1          5

(2) INFORMATION FOR SEQ ID NO:29:

(i) SEQUENCE CHARACTERISTICS:
        (A) LENGTH:  9 amino acids
        (B) TYPE:amino acid
        (C) TOPOLOGY:linear (ii) MOLECULE TYPE:peptide (iii) HYPOTHETICAL:yes (ix) FEATURE:
        (A) NAME/KEY:p939
        (B) OTHER INFORMATION:  synthetic peptide (xi) SEQUENCE DESCRIPTION:SEQ ID NO: 29:

Leu Ile Thr Val Ile Leu Gly Val Leu
  1               5

(2) INFORMATION FOR SEQ ID NO:30:

(i) SEQUENCE CHARACTERISTICS:
        (A) LENGTH:  9 amino acids
        (B) TYPE:amino acid
        (C) TOPOLOGY:linear (ii) MOLECULE TYPE:peptide (iii) HYPOTHETICAL:yes (ix) FEATURE:
        (A) NAME/KEY:p939
        (B) OTHER INFORMATION:  synthetic peptide (xi) SEQUENCE DESCRIPTION:SEQ ID NO: 30:

Leu Ile Thr Val Leu Ile Gly Val Leu
  1               5

(2) INFORMATION FOR SEQ ID NO:31:

(i) SEQUENCE CHARACTERISTICS:
        (A) LENGTH:9 amino acids
        (B) TYPE:amino acid
        (D) TOPOLOGY:linear (ii) MOLECULE TYPE:peptide (iii) HYPOTHETICAL:yes (ix) FEATURE:
        (A) NAME/KEY:p939
        (D) OTHER INFORMATION:synthetic peptide (xi) SEQUENCE DESCRIPTION:  SEQ ID NO: 31:

Ile Leu Thr Val Ile Leu Gly Val Leu
  1               5

(2) INFORMATION FOR SEQ ID NO:32:

(i) SEQUENCE CHARACTERISTICS:
        (A) LENGTH:  9 amino acids
        (B) TYPE:amino acid
        (C) TOPOLOGY:linear (ii) MOLECULE TYPE:peptide (iii) HYPOTHETICAL:yes (ix) FEATURE:
        (A) NAME/KEY:p939
        (B) OTHER INFORMATION:  synthetic peptide (xi) SEQUENCE DESCRIPTION:SEQ ID NO: 32:

Leu Leu Thr Val Leu Leu Gly Val Ile
  1               5

(2) INFORMATION FOR SEQ ID NO:33:

(i) SEQUENCE CHARACTERISTICS:
        (A) LENGTH:  9 amino acids
        (B) TYPE:amino acid
        (C) TOPOLOGY:linear (ii) MOLECULE TYPE:peptide (iii) HYPOTHETICAL:yes (ix) FEATURE:

-continued

```
            (A) NAME/KEY:p939
            (B) OTHER INFORMATION:  synthetic peptide (xi) SEQUENCE DESCRIPTION:SEQ ID NO: 33:

Leu Leu Thr Val Ile Leu Gly Val Leu
 1               5

(2) INFORMATION FOR SEQ ID NO:34:

(i) SEQUENCE CHARACTERISTICS:
            (A) LENGTH:  9 amino acids
            (B) TYPE:amino acid
            (C) TOPOLOGY:linear (ii) MOLECULE TYPE:peptide (iii) HYPOTHETICAL:yes (ix) FEATURE:
            (A) NAME/KEY:p939
            (B) OTHER INFORMATION:  synthetic peptide (xi) SEQUENCE DESCRIPTION:SEQ ID NO: 34:

Ile Leu Thr Val Leu Leu Gly Val Leu
 1               5

(2) INFORMATION FOR SEQ ID NO:35:

(i) SEQUENCE CHARACTERISTICS:
            (A) LENGTH:  9 amino acids
            (B) TYPE:amino acid
            (C) TOPOLOGY:linear (ii) MOLECULE TYPE:peptide (iii) HYPOTHETICAL:yes (ix) FEATURE:
            (A) NAME/KEY:p939
            (B) OTHER INFORMATION:  synthetic peptide (xi) SEQUENCE DESCRIPTION:SEQ ID NO: 35:

Leu Ile Thr Val Leu Leu Gly Val Leu
 1               5

(2) INFORMATION FOR SEQ ID NO:36:

(i) SEQUENCE CHARACTERISTICS:
            (A) LENGTH:9 amino acids
            (B) TYPE:amino acid
            (D) TOPOLOGY:linear (ii) MOLECULE TYPE:peptide (iii) HYPOTHETICAL:yes (ix) FEATURE:
            (A) NAME/KEY:p939
            (D) OTHER INFORMATION:synthetic peptide (xi) SEQUENCE DESCRIPTION:  SEQ ID NO: 36:

Leu Leu Thr Val Leu Ile Gly Val Leu
 1               5

(2) INFORMATION FOR SEQ ID NO:37:

(i) SEQUENCE CHARACTERISTICS:
            (A) LENGTH:  9 amino acids
            (B) TYPE:amino acid
            (C) TOPOLOGY:linear (ii) MOLECULE TYPE:peptide
```

(iii) HYPOTHETICAL:yes (ix) FEATURE:
                 (A) NAME/KEY:p939
                 (B) OTHER INFORMATION:  synthetic peptide (xi) SEQUENCE DESCRIPTION:SEQ ID NO: 37:

Leu Leu Thr Val Leu Leu Gly Val Leu
  1               5

(2) INFORMATION FOR SEQ ID NO:38:

(i) SEQUENCE CHARACTERISTICS:
                 (A) LENGTH:  9 amino acids
                 (B) TYPE:amino acid
                 (C) TOPOLOGY:linear (ii) MOLECULE TYPE:peptide (iii) HYPOTHETICAL:no (ix) FEATURE:
                 (A) NAME/KEY:p939/MART-1 32-40
                 (B) OTHER INFORMATION:  synthetic peptide (xi) SEQUENCE DESCRIPTION:SEQ ID NO: 38:

Ile Leu Thr Val Ile Leu Gly Val Leu
  1               5

(2) INFORMATION FOR SEQ ID NO:39:

(i) SEQUENCE CHARACTERISTICS:
                 (A) LENGTH:  9 amino acids
                 (B) TYPE:amino acid
                 (C) TOPOLOGY:linear (ii) MOLECULE TYPE:peptide (iii) HYPOTHETICAL:no (ix) FEATURE:
                 (A) NAME/KEY:gp100 280-288
                 (B) OTHER INFORMATION:  synthetic peptide (xi) SEQUENCE DESCRIPTION:SEQ ID NO: 39:

Tyr Leu Glu Pro Gly Pro Val Thr Ala
  1               5

(2) INFORMATION FOR SEQ ID NO:40:

(i) SEQUENCE CHARACTERISTICS:
                 (A) LENGTH:  10 amino acids
                 (B) TYPE:amino acid
                 (C) TOPOLOGY:linear (ii) MOLECULE TYPE:peptide (iii) HYPOTHETICAL:no (ix) FEATURE:
                 (A) NAME/KEY:HIV-nef 73-82
                 (B) OTHER INFORMATION:  synthetic peptide (xi) SEQUENCE DESCRIPTION:SEQ ID NO: 40:

Gln Val Pro Leu Arg Pro Met Thr Tyr Lys
  1               5                  10

(2) INFORMATION FOR SEQ ID NO:41:

(i) SEQUENCE CHARACTERISTICS:
                 (A) LENGTH:11 amino acids

-continued

```
            (B) TYPE:amino acid
            (D) TOPOLOGY:linear (ii) MOLECULE TYPE:peptide (iii) HYPOTHETICAL:no (ix) FEATURE:
            (A) NAME/KEY:p53 186-196
            (D) OTHER INFORMATION:synthetic peptide (xi) SEQUENCE DESCRIPTION:  SEQ ID NO: 41:

Asp Gly Leu Ala Pro Pro Gln His Leu Ile Arg
 1               5                  10

(2) INFORMATION FOR SEQ ID NO:42:

(i) SEQUENCE CHARACTERISTICS:
            (A) LENGTH:  9 amino acids
            (B) TYPE:amino acid
            (C) TOPOLOGY:linear (ii) MOLECULE TYPE:peptide (iii) HYPOTHETICAL:no (ix) FEATURE:
            (A) NAME/KEY:p53 264-272
            (B) OTHER INFORMATION:  synthetic peptide (xi) SEQUENCE DESCRIPTION:SEQ ID NO: 42:

Leu Leu Gly Arg Asn Ser Phe Glu Val
 1               5
```

ELUTION AND IDENTIFICATION OF T CELL EPITOPES FROM VIABLE CELLS

This is a continuation-in-part of copending application Ser. No. 08/011,007 filed on Jan. 29, 1993, abandoned.

ACKNOWLEDGEMENT

The present invention was developed in part with government support under grant number CA-57840 awarded by the National Institutes of Health. The government has certain rights in this invention.

FIELD OF THE INVENTION

The present invention relates generally to the elution of certain, preferably, immunogenic peptides and more particularly relates to the isolation of peptides associated with major histocompatibility complexes that are expressed at the cell surface of viable cells. Peptides eluted according to the invention may find use in the development of viral or tumor vaccines, or alternatively, as a means to treat autoimmune diseases. In particular, a naturally processed melanoma peptide recognized by CD8$^+$ cytotoxic T lymphocytes has been identified according to the present invention.

BACKGROUND OF THE INVENTION

T lymphocyte ("T cell") antigen receptors ("TCR") recognize endogenously processed fragments of antigens that are presented to T cells in association with major histocompatibility complex ("MHC") class I or class II molecules.

An individual's T cells recognize and are activated by protein antigens only if a fragment of the antigen is properly presented on the surface of a target cell. The antigen presentation process that allows an antigen to be recognized by a T cell requires that the antigen be associated with either (MHC) class I histocompatibility molecules for presentation to cytotoxic T lymphocytes ("CTLs") or class II histocompatibility molecules for presentation to helper T cells. Other T cell subsets such as γ/δ (gamma-delta) T cells (CD4$^-$, CD8$^-$) may recognize alternate "peptide presenting" molecules not encoded in the MHC, such as CD1, etc. The subset of T cells denoted CD8$^+$ recognize antigenic determinants/epitopes that are associated with class I histocompatability molecules. The other subset of T cells, CD4$^+$ cells, recognize antigenic determinants/epitopes that are associated with class II histocompatibility molecules. The antigenic determinants/epitopes that are presented on the surface of cells in association with MHC molecules are also known as T cell epitopes.

The study of CD8$^+$ T cell recognition of target cells has been extensive since the early 1970's when Zinkernagel and Doherty demonstrated that CTL recognition of viral-infected autologous target cells requires the presence of self class I MHC molecules. Thus such recognition of target cells by CD8$^+$ T cells is referred to as being MHC class I-restricted. Zinkernagel, R. M., et al., *Adv. Immunol.* 27:51 (1979); Doherty, P. C., et al., *Adv. Cancer Res.* 42:1 (1984); and Zinkernagel, R. M., et al., *Nature* 248:701 (1974), the disclosures of which are incorporated herein by reference. It was later shown that virus-specificity of CTL's is directed against viral protein-derived peptide sequences that are presented by infected cell MHC class I molecules to CD8$^+$ T cells. See, for example, Townsend, A., et al., *Cell* 42:457 (1985) and Townsend, A., et al., *Cell* 44:959 (1986), the disclosures of which are incorporated herein by reference.

As noted above, it is not the entire antigen that is presented by target cells and recognized by CD8$^+$ cells, but rather what is presented and recognized are small endogenously processed peptides that are generated from antigens by intracellular degradation pathways in either the cytosol or the endoplasmic reticulum ("ER") of the target cell. Such processed peptides bind to newly synthesized class I heavy chain-$\beta_2$-microglobulin heterodimers in the ER. See, for example, Yewdell, J. W., et al., *Science* 244:1072 (1989); Townsend, A., et al., *Cell* 62:285 (1990); and Nuchtern, J. G., et al., *Nature* 339:223 (1989), the disclosures of which are incorporated herein by reference. The processed peptide is bound to the class I heavy chain-light chain dimer molecule via the class I antigen binding site/peptide cleft. The complex thereby generated is a transport competent trimer as reported by Yewdell, J. W., et al., *Science* 244:1072 (1989); Townsend, A., et al., *Cell* 62:285 (1990); and Nuchtern, J. G., et al., *Nature* 339:223 (1989). This class I histocompatibility molecule-processed peptide complex is then expressed on the surface of the target cell where it may be ultimately recognized by T cell clonotypic receptors on CD8$^+$ cells in conjunction with CD8 accessory molecules. See, Rotzschke, O., et al., *Nature* 348:252 (1990); Van Bleek, G. M., et al., *Nature* 348:213 (1990); Rotzschke, O., et al., *Science* 249:283 (1990); and Falk, K., et al., *Nature* 348:248 (1990), the disclosures of which are incorporated herein by reference.

Recently, peptides have been isolated from the antigen binding sites of human and murine class I and class II molecules and directly sequenced. Two principal methods have been used to isolate such peptides. In one of the two methods total cellular extraction of such peptides is carried out in pH 2.0 trifluoroacetic acid ("TFA"). This method results in cell cytolysis and release of total cytosolic peptides, only a fraction of which are actually class I-related. This method also typically employs protease inhibitors since cell cytolysis results in the release of proteolytic enzymes that can alter or destroy peptides of potential interest. See, Rotzschke, O., et al., *Nature* 348:252 (1990), and Falk, K., et al., *Nature* 348:248 (1990), the disclosures of which are incorporated herein by reference. The second isolation method entails acid denaturation of immunoaffinity purified class I-peptide complexes. By contrast with the first method, the second method of peptide isolation is highly class I selective, and even class I allele specific since monoclonal antibodies directed against individual class I allotypes can be used to immunopurify class I complexes. By this latter approach, the majority of known class I-bound peptide sequence data has been acquired. See, for example, Van Bleek, G. M., et al., *Nature* 348:213 (1990); Rotzschke, O., et al., *Science* 249:283 (1990); Madden, D. R., et al., *Nature* 353:326 (1991); Jardetzky, T. S., et al., *Nature* 351:290 (1991); and Nikolic-Zugic, J., et al., *Immunol. Rev.* 10:54 (1991), the disclosures of which are incorporated herein by reference.

The main drawback of these two methods is that since both require cell cytolysis, a large number of starting cells ($10^9$–$10^{11}$) are required from which peptides are extracted after cellular cytolysis in order to obtain sequence grade quantities (approximately 1 pM) of specific peptide. Therefore the application of such techniques are limited to cell types which readily adapt to in vitro cell culture and which proliferate sufficiently well to allow such high cellular yields.

Methods of isolating class I peptide complexes are additionally relevant because CD8$^+$ lymphocytes have emerged as being potentially useful in the development of anti-tumor vaccines, which vaccines will ideally provoke anti-tumor immune responses in individuals. To that end, tumor infiltrating lymphocytes (TILs) have been found to be important agents in the generation of cellular immunity through their identification in spontaneously regressing lesions in some patients as reported by Kornstein, M. J., et al. *Cancer Res.* 43:2749 (1983), the disclosure of which is incorporated herein by reference. TILs are also frequently found in non-regressing lesions and when present in high numbers are correlated with a better clinical prognosis. Van Duinen, S. G., et al., *Cancer Res.* 48:1019 (1988), the disclosure of which is incorporated herein by reference. Numerous studies have shown that such TILs display potent anti-melanoma cytolytic activity when they are cultured in vitro with interleukin-2. See, for example, Lotze, M. T., *Pigment Cell* 10:163 (1990), and Rosenberg, S. A., et al., *N. Eng. J. Med.* 319:1676 (1988). Anti-melanoma cytolytic activity is typically associated with $CD8^+$ TIL subpopulations which recognize tumor cells in a class I-restricted manner. The HLA class I antigen, HLA-A2, appears to represent the most common class I restriction element for human melanoma TIL, however, other HLA class I antigens such as HLA-A1, -A10, -A24, -A31, -B44, -B50, and -CW7 have also been identified. The identification of such restriction elements may be important in the development of effective melanoma vaccines.

During the last several years, a number of further studies have been conducted on the autologous $CD8^+$ T cell-mediated response to human melanoma. See, for example, Parmiani, G., et al., *J. Natl. Cancer Inst.* 82:361 (1990) and Van den Eynde, B., et al., *Int. J. Cancer* 44:634 (1984), the disclosures of which are incorporated herein by reference. The emerging picture indicates that melanomas express multiple T cell epitopes, some of which are unique to a given tumor, while others are shared by allogeneic, HLA-matched melanomas. See, for example, Anichini, A., et al., *J. Immunol.* 142:3692 (1989); Wolfel, T., et al., *Eur. J. Immunol.* 24:759 (1994); and Crowley, N. J., et al., *J. Immunol.* 146:1692 (1991), the disclosures of which are incorporated herein by reference. These epitopes appear to represent short 9–10 amino acid peptides derived from tumor-associated antigens that are presented by MHC class I antigens to $CD8^+$ T cells. See, for example, Traversari, C., et al., *J. Exp. Med.* 176:1453 (1991) and Kawakami, Y., et al., *J. Exp. Med.* 180:347 (1994), the disclosures of which are incorporated herein by reference. While many class I alleles have been reported to represent restriction elements for tumor-reactive $CD8^+$ T cells, as reported by Hom, S. S., et al., *J. Immunother.* 10:153 (1991), the disclosure of which is incorporated herein by reference, the HLA-A2.1 allele, which is expressed by 45% of melanoma patients, appears to play an immunodominant role in presenting melanoma epitopes as reported by Crowley, N. J., et al., *J. Immunol.* 146:1692 (1991). As will be shown herein, at least six different $CD8^+$ T cell-defined epitopes appear to be expressed by multiple $HLA-A2^+$ melanomas. The identification and sequencing of these individual epitopes should allow for the design and testing of peptide-based immunotherapies for the treatment of melanoma.

It is difficult to extend the range of the search for biologically relevant allo-, viral-, and tumor-specific T cell epitopes to cell types that adapt poorly to tissue culture or which proliferate slowly in vitro. Accordingly there is a need for methods that will remove T cell epitopes from a greater range of cell types. In doing so, the development of peptide-based immunotherapies for the treatment of patients with melanoma and other diseases may be furthered.

SUMMARY OF THE INVENTION

Accordingly, it is a primary object of the present invention to provide a method of eluting MHC-bound peptides from the cell surface of viable cells that is non-toxic to the cells so that the cells can regenerate their MHC-peptide complexes.

Another object of the present invention is to provide a method of obtaining MHC-bound peptides that have a low affinity for MHC molecules.

Another object of the present invention is to provide a rapid method of removing MHC-bound peptides from viable cells.

Yet another object of the present invention is to provide a method of isolating MHC bound peptides from cells which are difficult to culture or propagate.

Still another object of the present invention is to provide a method of deriving multiple cell equivalents of MHC-bound peptides from a single cell.

Still yet another object of the present invention is to identify and characterize endogenously processed peptides presented by $HLA-A2^+$ melanomas that are recognized by class I-restricted, melanoma-specific $CD8^+$ T cells.

Another object of the present invention is to generate sufficient quantities of peptides eluted from MHC complexes for mass spectrometric sequencing and subsequent synthesis for vaccine development.

These and other objects of the present invention are achieved by one or more of the following embodiments.

In one aspect, the invention features a method of eluting peptides that are bound to major histocompatibility complex ("MHC") molecules expressed on the cell surfaces of viable cells that have at least one MHC-peptide complex presented on the surfaces of said cells, said method comprising:

incubating said cells in the presence of peptide elution buffer, and recovering said peptides from said peptide elution buffer.

In another aspect, the invention features a method of eluting increased amounts of MHC-associated peptides from one or more viable cells in culture that have expressed on their surfaces at least one MHC-peptide complex, comprising:

a. incubating said cells in the presence of peptide elution buffer at a pH in the range of about 2.7 to about 5.0 to elute said MHC-associated peptides from said cells;

b. harvesting the buffer eluate peptide-containing solution from step a);

c. neutralizing the acid remaining on said cell from said incubation;

d. reculturing said cell until such time that said cells have regenerated their MHC-peptide complexes; and e. repeating steps a-d one or more times to obtain additional amounts of MHC-associated peptides from said cells.

In preferred embodiments of the method, the peptide elution buffer comprises citrate-phosphate buffer with a pH in the range of about 2.5 to about 5.0, and more preferably, is iso-osmotic with a pH of about 3.3.

In other preferred embodiments of the invention, the incubation time is about 15 seconds to about 5 minutes, and more preferably, is about 15 seconds to one minute.

Other features and advantages of the invention will be apparent from the following description of the preferred embodiment, and from the claims.

DESCRIPTION OF THE DRAWINGS

FIG. 10A shows summation of the mass spectra obtained in the 500–1,600 m/z range. The (M+H)$^+$ ion at m/z=941 was selected for fragmentation to generate sequence data and used to generate a similar CID spectrum shown in FIG. 10B. Predicted and actual (underlined) masses for the fragments of the type b (carboxyl terminal cleavage) are shown above and type y (amino terminal cleavage) below the deduced sequence shown where X=isoleucine or leucine.

DETAILED DESCRIPTION OF THE INVENTION

I. Definitions

Figure 1:
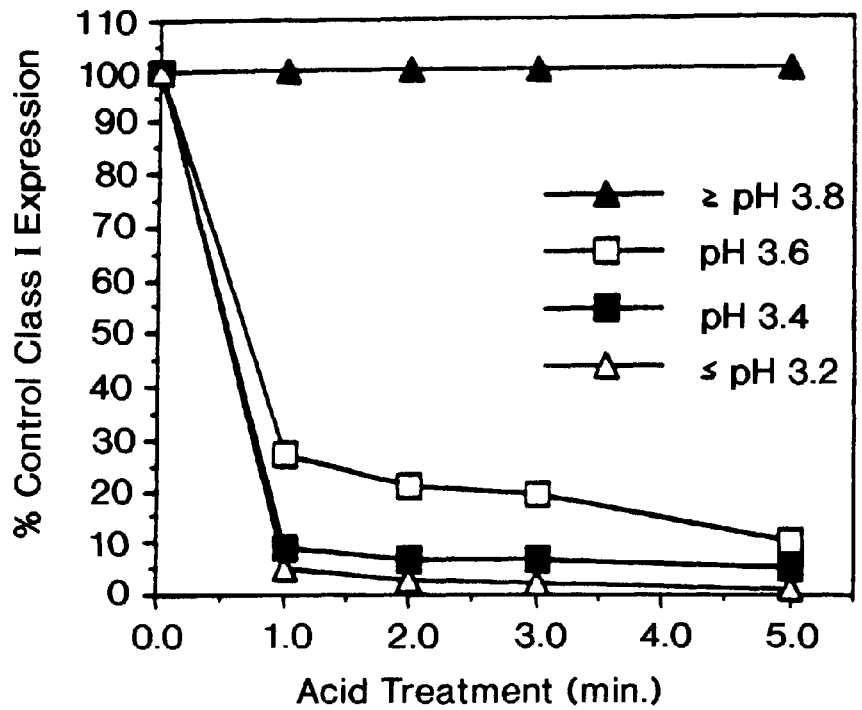
FIG. 1 shows the results of flow cytometry analysis of Mel 624 target cells that were treated with citrate-phosphate buffer at various pHs (3.0, 3.2, 3.4, 3.6, 3.8, 4.0 and 5.0) and assayed for class I molecule expression in indirect immunofluorescence assays using W6/32 monoclonal antibody. The results shown are the percentage of the W6/32 reactivity of peptide elution buffer-treated Mel 624 cells versus the W6/32 reactivity of control (untreated) Mel 624 cells.

As used herein, the term "Major Histocompatibility Complex (MHC)" refers to a genetic region found in all mammals whose products, including but not limited to class I and class II molecules, function in the presentation of peptides to effector T lymphocytes. In the human, this complex is denoted as HLA. In the mouse, this complex is denoted as H-2. Effector T cells are restricted by, and react to, autologous (self) MHC products. MHC molecules expressed on cells contain an antigen-binding site (ABS) in which peptides may be bound and presented to form "MHC-peptide complexes" and constitute "MHC-bound peptides." For example, "class I molecules" are presented to T cells and T cell recognition of such peptides is considered to occur in the context of such MHC molecules/complexes.

The term "antigen" is defined as a molecule which induces clonal lymphocytic proliferation and the generation of antigen-specific immunoglobulin from B lymphocytes and/or the generation of antigen-specific effector T lymphocytes.

"Epitope" or "antigenic determinant" refer to the relevant portion of an antigen that is recognized by effector cell receptors (i.e., immunoglobulin or T cell receptors). "T cell epitope" refers to a peptide that is presented on the cell surface of a target cell that is bound to an MHC gene product/molecule and is recognized by a T cell.

"Immunogenic" refers to the capacity of a substance or molecule (generally a protein or protein fragments (peptides)) to serve as an antigen.

"Peptide elution buffer" as used herein refers to the reagent solution that, when incubated in the presence of cells, results in the elution of previously MHC-bound T cell epitopes, i.e., peptides. In the present invention, the peptide elution buffer preferably is acidic, and more preferably has a pH of between about 2.7 and about 5.0. In the preferred embodiment, the peptide elution buffer is iso-osmotic, phosphate-citrate buffer of pH 3.3. Such extracted peptides may be subsequently isolated and analyzed biochemically.

The terms "peptide-loading" and "peptide pulsing" refer to the process by which exogenous peptides are incubated in the presence of target cells in order to establish an equilibrium that results in the occupation of MHC molecule antigen binding sites by these same exogenous peptides.

A "target" is a cell that elicits an effector cell response. Positive T effector cells only respond to target cells that express the relevant MHC-encoded gene products presenting relevant T cell epitopes.

The term "effector" or "effector cell" refers to a lymphocyte that mediates an antigen-specific response. The effector cell responses may include, but are not limited to, proliferation, cytotoxicity, and/or secretion of factors (immunoglobulin or cytokines by B cells, cytokines by T lymphocytes).

The terms "elute", "remove" "extract", and "strip" are used interchangeably to mean the physical removal or dissociation of T cell epitopes/peptides from MHC molecules expressed on the surface of viable cells.

"Viable" or "viability" refers to the maintenance of physical integrity of a cell and the ability of the cell to metabolically regenerate membrane components including MHC molecules after treatment with peptide elution buffer.

II. Methods—Acid Elution of Peptides

According to the present invention there is an improved and novel method of eluting MHC-bound peptides from the cell surface of viable cells which is rapid and which is non-toxic to the cells. Since cells are not killed in this process, they are able to regenerate their MHC-peptide complexes so that the regenerated MHC-bound peptides may be subsequently reeluted. The method uses far fewer cells than methods that employ cell cytolysis thereby expanding the range of cells from which such peptides may be isolated to cells which do not grow well in tissue culture or in vitro.

The method of the present invention may be carried out using any reagent solution that is capable of eluting MHC-bound peptides/T cell epitopes from the surface of viable cells without significantly affecting the viability of the cells (non-toxic). Therefore, cells so treated are able to reexpress MCH-peptide complexes. Preferably, the reagent solution is a peptide elution buffer which has an acidic pH, preferably between about 2.7 to about 5.0. Most preferably, the peptide elution buffer is iso-osmotic, citrate-phosphate buffer with pH 3.3. The MHC-bound peptides that are ultimately expressed on the surface of target cells are the result of either pulsing peptides onto the targets or infecting the target cells with a virus as described in detail below.

It is known, for example, that $CD8^+$ CTL's recognize HLA-A2 class I-presented immunogenic melanoma-specific peptide or peptides on the surface of $HLA-A2^+$ melanoma target cells. $CD4^+$ T cells may similarly recognize melanoma-specific peptides presented in the context of tumor class II molecules. Therefore the isolation and characterization of such melanoma-presented peptides may lead to the development of synthetic peptide vaccines capable of being used as an immunogen to elicit anti-melanoma T cell responses. Additionally, approaches to identify such peptides may have relevance in studies of immune reactivity to other tumor, viral or autoimmune systems where clear MHC-restricted T cell reactivities can be identified.

In the following example melanoma cells were treated with iso-osmotic, citrate-phosphate buffer at various acidic pHs to determine the kinetics and pH dependency of class I molecule expression. However, it should be readily apparent that the method of the present invention is not limited to use with melanoma cells. Indeed, the present invention may be employed with any cell bearing MHC determinants, such as, for example, colon carcinoma, squamous cell carcinoma, and gastric carcinoma.

EXAMPLE 1

Elution With Peptide Elution Buffer

The metastatic human melanoma Mel 624 ($HLA-A2^+$) cell line (a gift, available on request, from Dr. S. Rosenberg, National Institute of Health, Bethesda, Md.) was used as the prototypic target cell for treatment with the method of the present invention. This technique has been determined to be equally effective for elution of peptides from cultured cell lines as well as from fresh tissues.

The Mel 624 cells were cultured in tissue culture media ("TCM") consisting of RPMI-1640 media that was supplemented with 2 mM L-glutamine, 100 U/ml penicillin, 100 μg/ml streptomycin, 50 μg/ml gentamycin, and 10% heat-inactivated fetal calf serum. All regents were from Gibco, Grand Island, N.Y. The cells were incubated at 37° C. at 5% $CO_2$ in a humidified incubator. Mel 624 cells were grown in T225 flasks (Costar, Cambridge, Mass.). Single cell suspensions of the Mel 624 cells were generated by trypsinization of the cells using Trypsin-versene (Whittaker Bioproducts, Walkersville, Md.) followed by washing of the cells with TCM and Hank's Buffered Saline Solution ("HBSS") (Gibco). Adherent cell cultures may be treated either in situ in flasks or after adherent cells have been trypsinized and pelleted. Cells grown in suspension or cells derived from fresh tissue were pelleted and treated with peptide elution buffer. Trypsinization of target cells had no effect on the expression level of class I molecules prior to extraction or the sensitivity of cellular viability.

In order to cause virus-derived, class I-presented peptides to be expressed at target cell surfaces, Mel 624 target cells were infected with influenza A/UDORN. Influenza A/UDORN was a gift, and available upon request, from Dr. W. Biddison, National Institute of Health ("NIH") Bethesda, Md. and was grown in the allantoic sac of fertilized chicken eggs according to the method of McMichael, A. J., et al., Eur. *J. Immunol.* 8:705 (1978), the disclosure of which is incorporated herein by reference. The resulting harvested fluid contained influenza virus at a titer of $2 \times 10^8$ PFU/ml when it was assayed for cytopathic plaque formation on confluent monolayers of MDCK cells (ATCC accession No. CCL 34). Mel 624 tumor cells were infected with influenza A/UDORN at 1 PFU/cell in serum-free TCM for 1 hour. Heated-inactivated fetal calf serum was then added to the reaction mixture to a final concentration of 10%. The infected cultures were then incubated for an additional 18 hours at 37° C. in order to allow expression of virus-derived, class I-presented peptides at the target cell surface. At the end of the incubation time the cells were washed twice with HBSS.

Individual samples of $10^5$ trypsinized cells/sample were pelleted by centrifugation at 500×g for 5 minutes, or alternatively, cell lines to be extracted were left as adherent populations in T225 flasks. Target cell pellets or confluent flask-adherent cells ($2 \times 10^8$ total cells) were washed three times with 10 ml of HBSS in order to remove contaminant calf serum proteins. Residual HBSS was removed by aspiration after the final wash.

Citrate-phosphate buffers (0.131M Citric Acid/0.061M $Na_2HPO_4$, 290 mOsmol/kg $H_2O$ (iso-osmotic) was made essentially as outlined by the method of Suguwara, S., et al., *J. Immunol. Meth*. 100:83 (1987), the disclosure of which is incorporated herein by reference, except that 1% (w/v) bovine serum albumin (BSA) was not added in order to avoid molar excesses of contaminant BSA-derived peptides. The pH of the citrate-phosphate buffer (stock, unadjusted pH 3.0) was adjusted with 5N NaOH or 5N HCl to the desired final pH (pH 2.7–5.0), depending on the need of the particular study conducted.

To each sample of resuspended cells 100 μl of citrate-phosphate buffer at room temperature was then added at a pH of 3.0, 3.2, 3.4, 3.6, 3.8, 4.0 or 5.0 for the indicated time period (0–60 minutes). The buffer treated cells and the cell pellets were resuspended by gentle pipetting or by gently rocking flasks (5 ml/flasks) by hand for approximately 5 minutes. At the end of incubation, 3 ml of TCM containing 10% FBS was added to neutralize the acid in order to maintain extended cell viability. These volumes were found not to be critical; any volume sufficient to completely coat all sample cells was found to be effective. The cell suspensions were then pelleted (500×g for 3 min.) and the cell resulting cell-free supernatant was harvested. Alternatively, cell-free supernatants were removed from adherent cell preparations by pipet and the supernatants which contained eluted peptides were stored at −70° C. until fractionation procedures were performed later.

It was found that target cells survived the aforedescribed buffer treatment with no or very little loss of viability, as assessed by trypan blue exclusion, by rapidly neutralizing the cell pellets or flask-adherent cells with a 15 ml wash of TCM. The cell pellets were then resuspended in TCM or, in the case of flask cultures, the cells were recultured in a second aliquot of TCM. Target cells treated in such a way regenerated their class I MHC-peptide complexes within approximately 10–18 hours at which time they could be subjected to another round of peptide elution buffer stripping.

Antibodies

Target cells and donor peripheral blood lymphocytes (PBL's) were phenotyped for HLA-A2 expression using the BB7.2 anti-HLA-A2 (polymorphic) monoclonal antibody (MAb). The MAb was obtained by culturing BB7.2 hybridoma-ATCC accession number HB82. Total class I expression was monitored by the W6/32 anti-class I (monomorphic) monoclonal antibody (W6/32 hybridoma obtained from ATCC (accession number HB95)) The BBM.1 MAb was used to detect β-microglobulin, and the HC-10 MAb (Gillet, A. C., et al., *Eur. J. Immunol.* 20:759 (1990), the disclosure of which is incorporated by reference) was used to measure free, non-$β_2$-microglobulin associated, class I heavy chains (HC-10 hybridoma obtained from Dr. H. Ploegh, Massachusetts Institute of Technology, Cambridge, Mass., and available upon request. Total class II expression was determined using the L243 anti-HLA-DR (monomorphic) MAb. All MAbs, except for HC-10, were derived from hybridoma culture supernatants.

Immunofluorescence Assays

The neutralized cells were then assayed for class I molecule expression in indirect immunoflorescence assays using the MAbs described above according to the methods of Biddison, W. E., et al., *J. Immunol.* 129:730 (1982), and Mitchell, M. S. et al., *J. Clin. Oncol.* 10:1158 (1992), the disclosures of which are incorporated herein by reference. The W6/32 monoclonal antibody (anti-HLA class I, monomorphic determinant) was used along with a secondary FTIC-labeled goat anti-mouse IgG (F(ab')$_2$) (Organon Teknika, Durham, N.C.). HC-10 was used as a 1/500 dilution of ascites in HBSS. The assays were monitored by flow cytometry performed on a FACScan flow cytometer (Becton Dickinson, Mountainview, Calif.) with reactivity expressed in mean fluorescence channel (MFC) units. The gain setting (laser amplifier) is set by the operator each time the cytometer is run based on a negative control sample. Since this control varies from run to run, the MFC scale is arbitrarily set for each run, although within each run the fluorescense scale is uniform and proportional.

The results of treatment of Mel 624 cells with peptide elution buffer shown in FIG. 1 are reported as the percentage of the W6/32 MFC reactivity of treated cells versus the W6/32 MFC reactivity of control, untreated, Mel 624 cells. Treatment of Mel 624 cells with citrate-phosphate buffer with pH≦3.8 resulted in a rapid, ≦1 minute, denaturation of class I complexes as measured by W6/32 reactivity. Treatment of Mel 624 target cells with citrate-phosphate buffer with a pH≧3.8 had minimal effect on the level of expression of W6/32 reactive class I species Class II complexes undergo confromational changes at or below pH 4.5. Gorga, J. C., et al., *Crit. Rev. Immunol.* 11:305 (1992), the disclosure of which is incorporated herein by reference.

In the following example the viability of cells treated with citrate-phosphate buffer was assessed.

EXAMPLE 2

Figure 2:
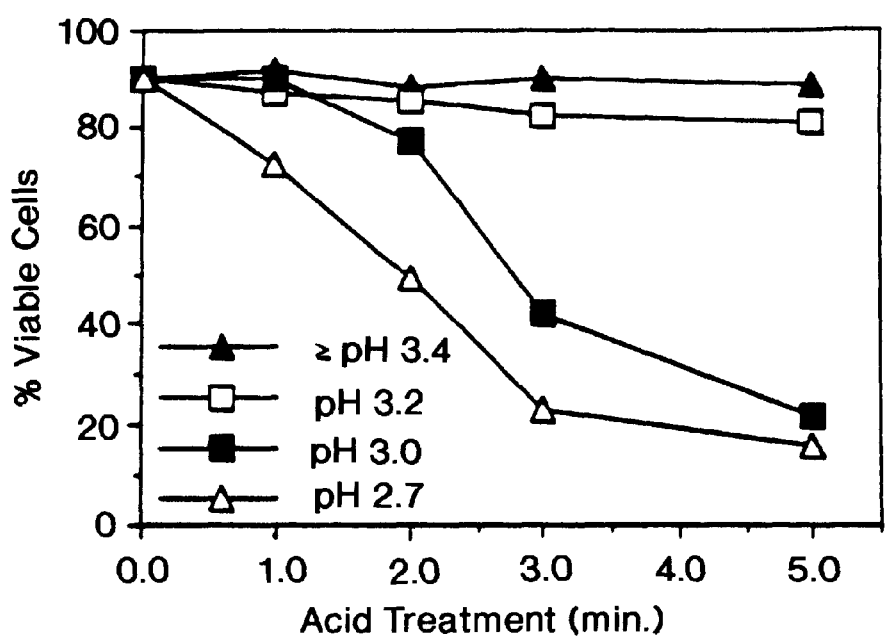
FIG. 2 is a graph showing results of studies of Mel 624 target cell viability upon treatment of the cells with citrate-phosphate buffer at pHs of 2.7, 3.0, 3.2, and $\geq 3.4$ (3.4, 3.6, 3.8, 4.0, 5.0) for time intervals up to five minutes.

Mel 624 target cells were treated as in Example 1 with iso-osmotic, citrate-phosphate buffer at pHs of 2.7, 3.0, 3.2, 3.4, 3.6, 3.8, 4.0, and 5.0. Cells were assessed for their viability by monitoring trypan blue dye exclusion in incubations of 1–2 minutes. As shown in FIG. 2, citrate-phosphate buffers with pH<3.2 were toxic to Mel 624 target cells in incubations exceeding 1–2 minutes. Incubations carried out in buffers with pH≧3.2 were well tolerated by the cells and did not lead to significant cell death ever after 5 minutes of treatment. In order to optimize the class I denaturing effects as well as cell viability, iso-osmotic, citrate-phosphate buffer at a pH of 3.3 was used for all subsequent studies.

The sensitivity of class I molecules expressed by diverse cell types was determined in the following example.

EXAMPLE 3

Tumor cell lines used were melanoma cell lines Mel 397 (HLA-A2-) and Mel 624 (HLA-A2$^+$) (gifts, available on request, from Dr. S. Rosenberg, NIH), PCI-50 squamous cell carcinoma, HR gastric carcinoma (gifts, available on request, from Dr. T. Whiteside, Pittsburgh Cancer Institute, Pittsburgh, Pa.) and the EBV-transformed B cell lines K4B (HLA-A2$^+$ (gift, available on request, from Dr. Biddison, NIH), C1R.A2 (an HLA-A2$^+$ transfectant of the HLA-A,B null C1R cell line as described by Storkus, W. J. et al., *Proc. Natl. Acad. Sci. USA* 88:5989 (1991), the disclosure of which is incorporated herein by reference, and C1R.Bw58 (an HLA-BW58$^+$ transfectant of the HLA-A,B null C1R cell line as described by Storkus, W. J., et al., *Proc. Natl. Acad. Sci. USA* 86:2361 (1989). All tumor cell lines were cultured in TCM as described in Example 1.

Figure 3:
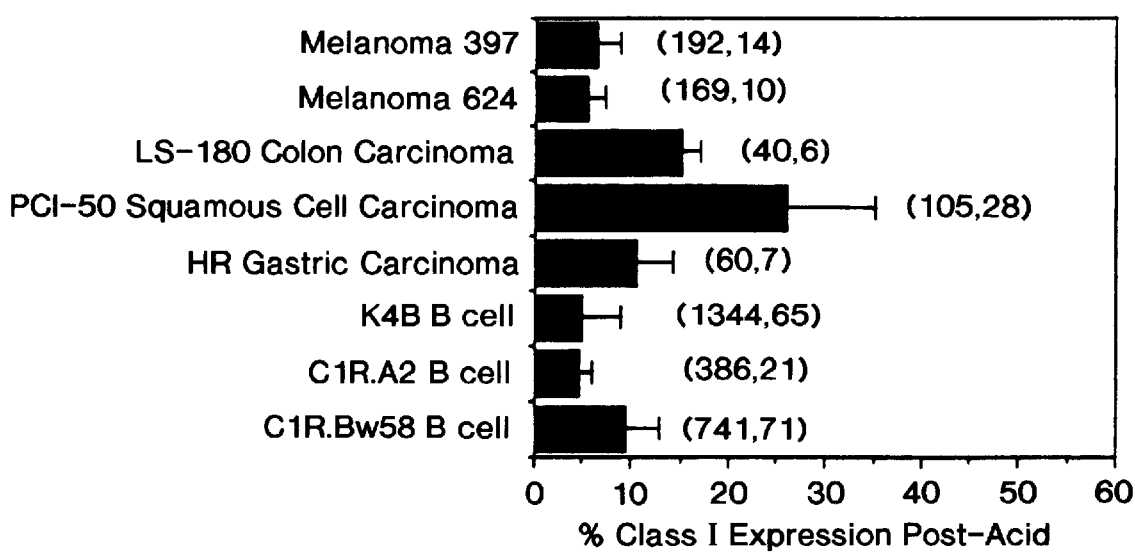
FIG. 3 is a graph showing results of flow cytometry analyses of various tumor cell lines that were treated with iso-osmotic, pH 3.3 citrate-phosphate buffer for 1 minute and then assayed for class I molecule expression in indirect immunofluorescence assays using W6/32 monoclonal antibody. The results shown are the mean standard deviation of the percentage of the W6/32 reactivity of the peptide elution buffer-treated cells versus the W6/32 reactivity of control cells. Pre-and post treatment W6/32 reactivity mean fluorescence channel values are in parenthesis.

The various tumor cells were treated with pH 3.3 iso-osmotic, citrate-phosphate buffer for one minute followed by neutralization and flow cytometric analysis of class I molecule expression using the W6/32 monoclonal antibody as described in Example 1. The results, shown in FIG. 3, show that in all cases, treatment greatly reduced cellular reactivity with the W6/32 monoclonal antibody within the 1 minute reaction time. Approximately 85–95% of W6/32 reactive class I species were removed on all the target lines that were tested, with the possible exception of the PCI-50 squamous cell carcinoma line which exhibited an approximately 74% reduction. Treatment with peptide elution buffer appeared to decrease the expression of both HLA-A and HLA-B locus class I determinants equally well since both the C1R.A2 and C1R.Bw58 transfected cell lines which express only the HLA-A2 or HLA-Bw58 class I molecules, respectively, appeared to be similarly affected by pH 3.3 treatment. Such lack of differential sensitivity of the present method of the claimed invention with respect to the type of class I molecule, HLA-A, HLA-B, or HLA-C was also supported in view of the near absolute reduction in W6/32 reactivity of heterozygous class I expressing target cells such as Mel 624 (HLA-A2, -A3, -B7, -B14, -Cw7) or K4B (HLA-A1, -A2, -B7, -B8) after these cells were treated for 1 minute at pH 3.3.

While the foregoing results show that treatment with peptide elution buffer greatly reduces cellular reactivity with the W6/32 Ab which recognizes a monomorphic combinatorial determinant requiring class I heavy chain-$\beta_2$-microglobin ($\beta_2$M), it was not clear whether the individual class I heavy and light chains ($\beta_2$m) remained cell associated. In the following example the association of the heavy and light chains was determined upon treatment.

EXAMPLE 4

Single cell suspensions of Mel 624 cells were generated by trypsinization and washing as described in Example 1. The resulting cells were partitioned into four $10^6$ cell fractions and treated with pH 3.3 iso-osmotic, citrate-phosphate buffer for 0, 15, 30, or 60 seconds. The samples were then neutralized by addition of TCM and washing and pelleted by centrifugation at 500×g for 5 minutes. Indirect immunofluorescense assays were performed as in Example 1 using primary monoclonal reagents and a FITC-conjugated F(ab')$_2$ goat anti-mouse IgG (Organon Teknika). The following primary monoclonal reagents were used: W6/32, HC-10, BBM-1, L234, and a negative control, primary antibody OKT3 which is non-reactive with the Mel 624 target cells. HC-10 was used as 1/500 dilution of ascites in HBSS. Indirect immunofluorescence assays were performed as described in Example 1. The results shown below in Table 1 are reported as mean fluorescence channel number (MFC) units.

TABLE 1

| Time of pH 3.3 Treatment | MAb Reactivity (MFC) | | | | |
|---|---|---|---|---|---|
| (control) (sec) | W6/32 (H + $\beta_2$m) | BBM-1 ($\beta_2$m) | HC-10 (free H) | L243 (HLA-DR) | OKT3 |
| 0 | 169 | 67 | 9 | 477 | 8 |
| 15 | 36 | 18 | 60 | 565 | 10 |
| 30 | 18 | 19 | 60 | 522 | 10 |
| 60 | 18 | 17 | 71 | 529 | 9 |

H = heavy chain; $\beta_2$m = $\beta_2$ microglobulin; HLA-DR = class II molecule.

The above results show that treatment of Mel 624 target cells with pH 3.3. citrate-phosphate buffer led to the rapid loss of reactivity (15–30 seconds) with both the W6/32 and BBM-1 MAbs, the gain of reactivity with HC-10, and no change of reactivity with the L234 monoclonal reagent. Longer buffer treatments were not determined to lead to any significant further denaturation of class I complexes. Such results indicate that class I heavy chains remain associated with the cell surface in pH 3.3 buffer, but that $\beta_2$m is lost into the cell-free supernatant. As previously reported by Suguwara, S., et al., *J. Immunol. Meth.* 100:83 (1987), the disclosure of which is incorporated herein by reference, class II molecules that are recognized by the L243 reagent were not affected by cellular peptide elution buffer treatments as low as pH 3.0.

While the foregoing results suggest that there is a qualitative loss of native class I molecules on peptide elution buffer-treated target cell membranes, CD8$^+$ T cell recognition of target cells bearing the appropriate class I restricting element serves as a much more sensitive index of limiting class I molecule expression. In the following example cytotoxic T lymphocyte (CTL) recognition of target cells after treatment according to the methods of the present invention was examined.

EXAMPLE 5

Anti-influenza peptide CTL lines were generated by the method of Carbone, F. R., et al., *J. Exp. Med.* 167:1767 (1988), the disclosure of which is incorporated herein by reference. Briefly, 40–60×10$^6$ peripheral blood lymphocytes (PBLs) were obtained from normal, healthy HLA-A2$^+$ donors by venipuncture. Ficoll-Hypaque separations were then performed using the lymphocyte separation medium (LSM) kit according to the manufacturer's protocol (Organon Teknika). Peripheral blood primary stimulations were performed as follows: the lymphocytes were cultured in 10 ml of AIM-V media (Gibco) for 7 days that contained 25 µg/ml of the synthetic influenza matrix nonameric peptide Flu M1 57–68 (KGILGFVFTLTV--Lys-Gly-Ile-Leu-Gly-Phe-Val-Phe-Thr-Leu-Thr-Val) (SEQ ID NO: 1) which was synthesized by the Peptide Synthesis Facility, Shared Resource, Pittsburgh Cancer Institute, Pittsburgh, Pa. Weekly restimulations were then performed by taking 5×10$^6$ viable responders and adding 10$^7$ irradiated (3,000 rad) HLA-A2$^+$ allogeneic PBLs in 10 ml of AIM-V media supplemented with 25 µg/ml Flu M1 peptide plus 50 IU/ml rhIL-2 (Chiron, Emeryville, Calif.). Fresh AIM-V media with 50 IU/ml rhIL-2 was added to rapidly proliferating T cell cultures as was needed. The GL1 anti-Flu CTL line was selected for use after tertiary boosting and after display of specific recognition of Flu M1 peptide that was presented in the context of HLA-A2 expressed by melanoma or B cell targets. GL1 lysed both influenza A/UDORN infected HLA-A2$^+$ targets or Flu M1 peptide-pulsed HLA-A2$^+$ targets, but not control uninfected or non-peptide pulsed targets (data not shown).

The influenza A (Flu M1 57–68) peptide specific, HLA-A2-restricted CD8$^+$ CTL effector line (GL1) as generated according to the foregoing description was investigated to see if such a CTL effector line could recognize influenza infected Mel 624 target cells that were treated with peptide elution buffer according to the methods of the present invention.

Mel 397 (HLA-A2$^-$) and Mel 397 (HLA-A2$^+$) were mock infected (treated with TCM only) or infected with influenza A/UDORN at 1 pfu/cell for 18 hours at 37° C. as described above. 1–2×10$^6$ infected cells were then trypsinized, washed with TCM, and pelleted by centrifugation. The cells of both cell lines were then labeled with 100 µCi of Na$_2$$^{51}$CrO$_4$ (New England Nuclear, Boston, Mass.) by incubating for 1 hour at 37° C. The cells were then washed twice with HBSS to remove free label and treated with either HBSS at pH 7.4 or iso-osmotic, citrate-phosphate buffer at pH 3.3 for 1 minute. TCM was then added to the treated cells to neutralize the acid.

Some buffer-extracted targets were allowed to regenerate their class I-peptide complexes by subsequently culturing the cells at 37° C. for up to 18 hours in TCM that contained 100 µCi Na$_2$$^{51}$CrO$_4$. A portion of these regenerated target cells were treated a second time with pH 3.3 citrate-phosphate buffer.

Standard 4 hour cytotoxicity assays with GL1 CTL effector cells were then carried out on the various groups of treated target cells after the cells were neutralized of acid by washing with TCM followed by HBS. In order to perform the assays 100 μl of target cells were loaded into each assay well of 96-well U-bottomed microculture wells at $10^4$ targets/well. Direct target sensitivity to GL1 (anti-Flu M1 peptide-specific, HLA-A2-restricted) CTL was assessed by adding GL1 effector cells at an effector-to-target ratio of 1:1. The cells were then incubated for 4 hours at 37° C. The control, spontaneous release, constituted target cells and TCM only (for assays involving peptides this constituted 100 μl of target cells plus 125 μl of TCM; if no peptides were involved, targets and TCM were used at 100 μl each). The maximum release control consisted of $10^4$ target cells plus 100 μl of Triton X-100 (Sigma, St. Louis Mo. (10% in ddH$_2$O)) in directed assays or 125 μl of Triton X-100 in peptide pulsing assays. After the 4 hour incubation, the contents of the 96-well plates were centrifuged at 50×g for 5 minutes to pellet the cells, and 100 μl of supernatant was harvested for counting in an LKB gamma counter (Pharmacia, Piscataway, N.J.).

In the following table the percent specific lysis for these studies was calculated as (Experimental cpm-Spontaneous cpm)/(Maximum cpm-Spontaneous cpm)×100%. Spontaneous release in all cases was always less than 15% of the maximal release for all targets assessed.

C. as described in Example 1. The influenza-infected cells and control (uninfected) Mel 624 target cells were then treated with pH 3.3 iso-osmotic citrate-phosphate buffer for 1 minute as described in Example 1 in situ while still adherent to T225 culture flasks. The peptides in the resulting cell-free, buffer-extracted supernatant were isolated by concentrating and desalting the supernatant on SepPak C$_{18}$ cartridges (Millipore, Bedford, Mass.) according to the manufacturer's protocols. In brief, columns were attached to 5 cc syringes (Becton-Dickinson, Rutherford, N.J.) and prewashed with 2–3 ml of acetonitrile (Fisher Scientific, Pittsburgh, Pa.) and then washed with 2–3 ml of ddH$_2$O. Buffer extracts were then loaded into the syringes and the extracts were allowed to gravity elute through the SepPak cartridges. The peptide-loaded columns were then washed with 5 ml of ddH$_2$O and the bound material was eluted with 1–2 ml of 60% acetonitrile/40% ddH$_2$O. The eluted material was then lyophilized in a Savant SpeedVac (Farmingdale, N.Y.) to near complete dryness with approximately 10 μl of residual fluid remaining, and then reconstituted in 0.5 ml of iso-osmotic, citrate-phosphate buffer at pH 3.3. Peptides that were ≦3,000 Mr. were then isolated by fractionation on Centricon-3 ultrafiltration devices (Amicon, Cambridge, Mass.) according to the manufacturer's protocols by centrifugation at 2000×g for 1–2 h. The resulting bulk peptides were then fractionated by liquid chromatography (LC),

TABLE 2

| Target | HLA-A2 (+/−) | Flu (+/−) | Primary pH 3.3 Treatment/ Regenerate for: | | | Secondary pH 3.3 Treatment | GL1 % Specific Lysis (E/21) |
|---|---|---|---|---|---|---|---|
| | | | 0 h | 4 h | 18 h | | |
| Mel 397 | − | − | − | − | − | − | 4 |
| | − | + | − | − | − | − | 7 |
| | − | + | + | − | − | − | 1 |
| | − | + | − | + | − | − | 0 |
| | − | + | − | − | + | − | 1 |
| | − | + | − | − | + | + | 2 |
| Mel 624 | + | − | − | − | − | − | 5 |
| | + | + | − | − | − | − | 20 |
| | + | + | + | − | − | − | 1 |
| | + | + | − | + | − | − | 0 |
| | + | + | − | − | + | − | 26 |
| | + | + | − | − | + | + | 1 |

As shown in Table 2, Mel 624 (HLA-A2$^+$) targets were recognized and lysed by GL1 effector cells after influenza infection. Recognition of targets by the GL1 cells was destroyed by pH 3.3 treatment, but such recognition was regenerated after 18 hours of incubation in TCM at 37° C. Regeneration did not take place after only 4 hours of incubation. The regenerated recognition or sensitivity to GL1 CTL-mediated lysis was destroyed by a second pH 3.3 treatment. Mel 397 (HLA-A2$^−$) cells were not recognized by the HLA-A2 restricted GL1 CTL under any of the conditions the cells were subjected to.

As shown in the preceding example GL1 CTL were unable to recognize influenza-infected Mel 624 target cells that were treated with peptide elution buffer according to the methods of the present invention. This finding, coupled with the acid-associated loss of β$_2$m, suggested that the class I-bound peptides (CD8$^+$ T cell epitopes) might also be released from the surface of cells treated with peptide elution buffer as presently described. In the following example, this possibility was explored.

EXAMPLE 6

2×10$^8$ Mel 624 cells in T225 culture flasks were infected with influenza A/UDORN at 1 pfu/cell for 18 hours at 37° preferably reverse phase high performance liquid chromatography (RP-HPLC), as described herein.

Figure 4A:
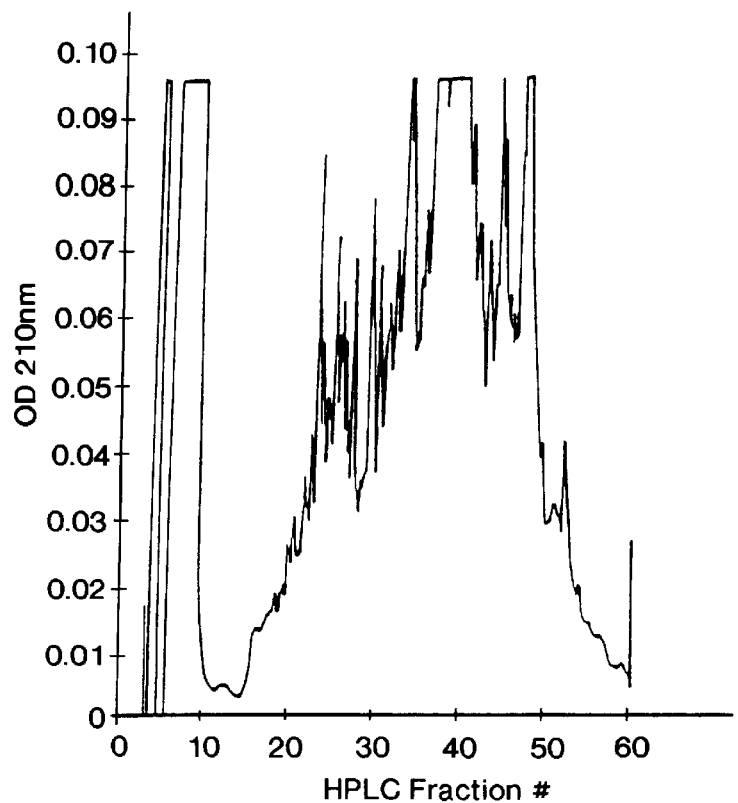
FIG. 4A is an RP-HPLC chromatogram of endogenously processed peptides that were eluted from influenza A/UDORN-infected Mel 624 cells that were treated with iso-osmotic, pH 3.3 citrate-phosphate buffer according to the present invention and monitored at 210 nm.

Briefly, the bulk peptides were fractionated on a C$_{18}$ reverse-phase (RP) column (Alltech, Deerfield, Ill.) using an Eldex, (San Carlos, Calif.) programmable pump in a 99.92% water/0.08% trifluoroacetic acid (TFA) to 39.935 water/ 0.07% TFA/60% acetonitrile gradient. The flow rate was maintained at 1.0 ml/minute and 1 ml fractions were collected. Each incremental gradient was linear. The HPLC runs were monitored for peptides species by monitoring the absorbence of the peptides at 210 nm using a multi-diode array detector (Linear UVIS, Reno, Nev.). The resulting HPLC fractions were transferred to Eppendorf polypropylene tubes and lyophilized. The results of the RP-HPLC are shown in FIG. 4A.

Figure 4B:
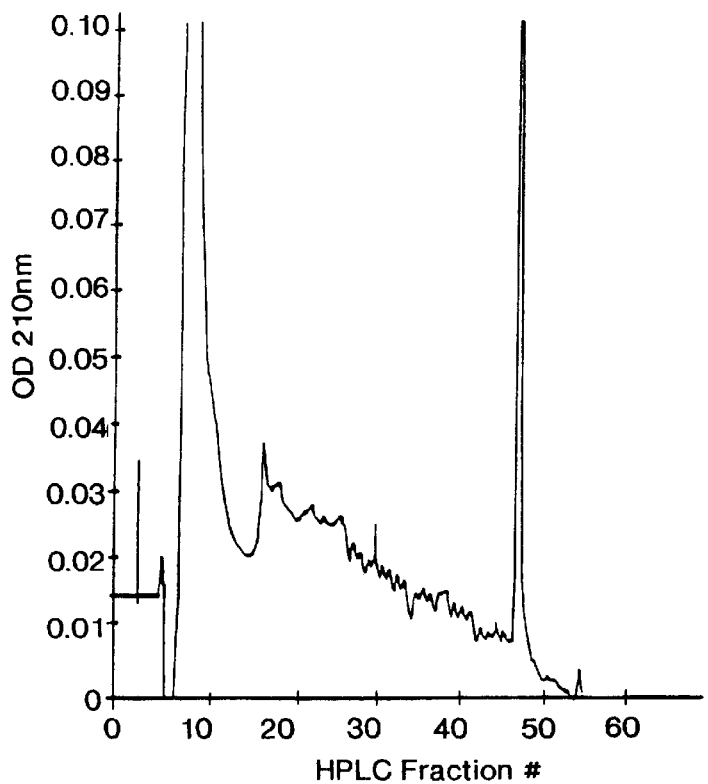
FIG. 4B is an RP-HPLC chromatogram of the synthetic peptide Flu M1 58–66.

Since influenza A infection of HLA-A2$^+$ target cells had been previously shown to result in the endogenous processing and presentation of the immunodominant Flu M1 58–66 sequence, and the GL1 CTL line was primed against a peptide containing this sequence (i.e., Flu M1 57–68), synthetic Flu M1 58–66 peptide was also fractionated by HPLC. The Flu M1 sequence eluted in HPLC fractions 47 and 48 (47–48% acetonitrile) is shown in FIG. 4B.

EXAMPLE 7

$2\times10^8$ Mel 624 cells were infected with influenza A/UDORN as described in the protocol for Example 5. The infected cells and an equivalent number of control cells (uninfected) were treated with pH 3.3 iso-osmotic, citrate-phosphate buffer. The eluted peptides were fractionated by HPLC as described in Example 6. The individual melanoma-derived HPLC peptide fractions were lyhophilized to remove organic solvents and then resuspended in pH 7.4 HBSS. Aliquots of these fractions were then pulsed onto K4B (HLA-A2$^+$) B cell targets that had previously been labeled with $^{51}$Cr. The K4B cells were then allowed to express class I molecules by incubation of the targets at 37° C. for 1 hour. GL1 (anti-Flu M1 56–68 peptide-specific, HLA-A2 restricted) CTL were added to microculture wells of 96 well microculture dishes at an effector-to-target cell ratio of 1:1. The CTL's and targets were incubated for 4 hours at 37° C. in cytotoxicity assays performed as described in Example 1.

Figure 5:
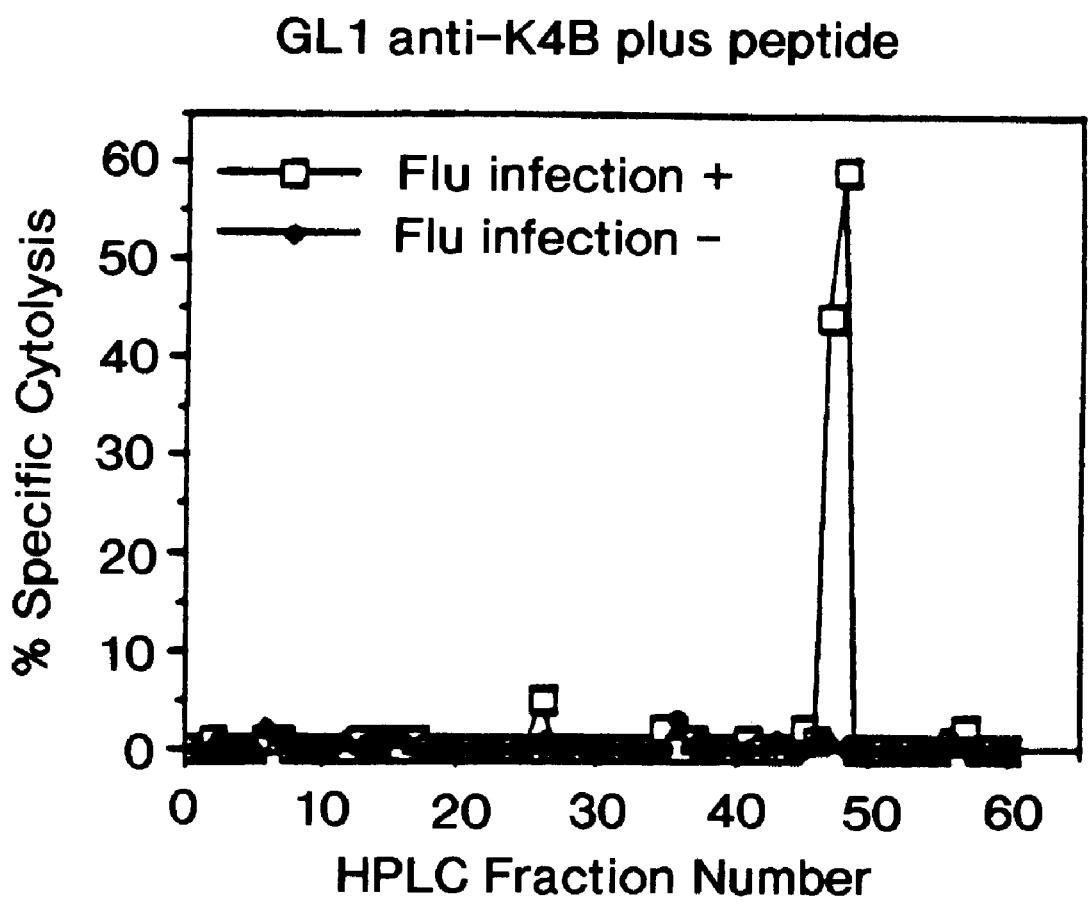
FIG. 5 is a graph showing the results of cytotoxicity assays in which iso-osmotic, pH 3.3 citrate-phosphate elution of influenza A/UDORN-infected Mel 624 cells was performed, the eluted peptides were fractionated by HPLC, the peptides from individual fractions were pulsed onto $^{51}$Cr-labeled K4B B cell targets, and GL1 CTL effector cells were added. Percent specific cytolysis as a function of HPLC fraction number is reported.

The results of these studies as shown in FIG. 5 are reported as percentage of specific K4B cytolysis. As can be seen, only K4B target cells that were incubated with peptides eluting in fractions 47 and 48 derived from influenza-infected Mel 624 cells were lysed by GL1 effector cells. The analagous fractions derived from uninfected Mel 624 cells were unable to confer susceptibility to GL1 CTL-mediated lysis on K4B target cells. The temporal co-elution of the synthetic Flu M1 57–68 peptide and the endogenously processed peptide derived from influenza-infected Mel 624 targets (recognized by GL1 CTL) in HPLC fractions 47/48 strongly suggests the identity of these peptide species. Additionally mass spectrometric analysis has showed that fraction 48 contained an endogenously processed peptide of molecular weight 968 having the sequence GXXGFVFTX (where X=I or L) (SEQ ID NOS: 2–5) which is completely consistent with the Flu M1 58–66 sequence.

The elution and identification of the endogenously processed, HLA-A2-presented Flu M1 58–66 sequence from HLA-A2$^+$ influenza virus-infected target cells indicates the feasibility and utility of using the present method for isolating and identifying other endogenously processed MHC-presented peptides.

The remaining examples in this section demonstrate that peptides eluted from class I molecules expressed by HLA-A2$^+$ melanoma cell lines according to the methods of the present invention contain tumor infiltrating lymphocyte (TIL) reactive T cell epitopes.

EXAMPLE 8

The tumor cell lines used were grown in T225 flasks in TCM and were maintained as described in Example 1. The metastatic melanoma cell lines included: Mel 397 (HLA-A2$^-$); Mel 526 (HLA-A2$^+$); Mel 624 (HLA-A2$^+$); Mel 392.A2 (an HLA-A2$^+$ transfectant of Mel 397 which was a gift, and available on request, from Dr. Yutaka Kawakami, NIH as described in Kawakami, Y., et al., *J. Immunol.* 148:638 (1992), the disclosure of which is incorporated herein by reference); and WM35 (HLA-A2$^+$) which was a gift, and available on request, from Dr. M. Herlyn, Wistar Institute. The following EBV-transformed B cell lines were also used: K4B (HLA-A2$^+$), and the C1R series of class I transfectants C1R.A2, C1R.A3, C1R.Aw68, C1R.Aw69, C1R.B7, and C1R.BwS8. See, Storkus, W. J., et al., *Proc. Nat'l Acad. Sci. USA* 86:2361 (1989); Storkus, W. J., et al., *Proc. Nat'l Acad. Sci. USA* 88:5989 (1991); and Storkus, W. J., et al., *J. Immunol* 143:3853 (1989), the disclosures of which are incorporated herein by reference. The C1R transfectant cells express a class I molecule composition that is made up of approximately 90–97% of the transfected class I allele and 3–10% of the endogenous Cw4 allele.

Tumor infiltrating lymphocyte (TIL) lines were maintained in RPMI-1640 that was supplemented with 10% heat-inactivated human AB pooled serum (Gibco), the antibiotics used in TCM, and 6000 IU/ml rhIL-2 (Chiron). Oligoclonal TIL lines used in these studies were TIL 1074 and TIL 1128 which were provided by, and available on request, from Dr. Y. Kawakami, NIH, and the TIL E92-19 that was developed in the Immunologic Monitoring and Diagnostic Laboratory (IMDL) at the Pittsburgh Cancer Institute, and available on request. Each of these oligoclonal TIL lines ($\geq$88% CD8$^+$) displayed HLA-A2 restricted, melanoma-specific cytotoxicity in 4 hour $^{51}$Cr-release assays.

Peptides were extracted from the melanoma cell lines as described in the previous examples. Briefly, melanoma cell lines were grown until they were approximated 80% confluent in T225 flasks with approximated 40–45$\times$10$^6$ cells per flasks. TCM was then removed and the adherent monolayer of cells was washed 2–3 times with HBSS and removed by pipet, and 5 ml of pH 3.3 iso-osmotic, citrate-phosphate buffer was then added to the flasks, and the cells were incubated for 1 minute at room temperature. The peptide elution buffer solution containing the peptides previously bound to the class I molecules on the cell surfaces was harvested by pipet, centrifuged to remove any viable cells present and the resulting cell-free supernatant was stored at $-70°$ C.

The treated cell monolayers were then briefly washed with 40–50 ml of serum-free TCM and then were decanted. The cells were recultured in 75 ml of TCM. The cells remained approximately 90–95% viable after treatment with peptide elution buffer and the cells regenerated their class I peptide complexes after an additional 10–18 hours of incubation at 30° C. The same flasks were routinely harvested for melanoma peptides on a daily basis by using the peptide elution buffer ("acid") elution protocol set forth herein. After 3–4 days, the cells were passaged ⅕ into new T225 flasks and the daily acid elutions were continued, resulting in multiple cell equivalents of class I-associated peptide being extracted from a single cell over the course of several days. In these studies, approximately 2$\times$10$^9$ melanoma cells were repetitively stripped of their class I-associated peptides for 4 days and the resulting peptides were then fractionated. Day 2–3 yields of peptides resulting from stripping typically exceeded the day 1 yield by 9–116% as shown in Table 3.

TABLE 3

| Peptide Yield ($\mu$g) Per Day | | % Day 1 Yield |
|---|---|---|
| Day 1 | 5.45 | 100 |
| Day 2 | 12.16 | 216 |
| Day 3 | 5.88 | 109 |
| Day 4 | 6.65 | 122 |

The daily buffer eluates that contained peptides derived from a single melanoma line were combined. The combined eluates were loaded onto C$_{18}$ SepPak devices as described above. The peptides were eluted from the columns by 1–2 ml of 60% acetonitrile in water and then lyophilized to remove the organic solvent. The samples were then reconstituted in 1 ml of pH 3.3 iso-osmotic, citrate-phosphate buffer and the reconstituted solution was fractionated on a Centricon-3 ultrafiltration device according to the manufacturer's protocol. The flowthrough from the Centricon-3 device consisted of peptides ≦3,000 Mr (approximately 30 amino acids in length) and the flowthrough was HPLC fractionated as described above. The solvents used for HPLC were A: 99.9% water/0.08% TFA, B: 99.94% acetonitrile/0.06% TFA. The gradients used in the HPLC were the following linear step intervals: isocratic A solvent for 0–5 minutes; 0% B (in A) to 10% B (in A) from 5–10 minutes; and 10% B (in A) to 35% B (in A) from 10–60 minutes. The flow rate used was 0.8 ml/minute and 0.8 ml fractions were collected. Individual HPLC fractions were lyophilized to remove organic solvents and then the fractions were reconstituted in 200 μl of HBSS and stored at −20° C. until the fractions were used in cytotoxicity assays.

Four or five hour cytotoxicity assays were performed as described above in Example 5. Briefly, melanoma cell lines were trypsinized, washed in TCM, pelleted by centrifugation, and labeled with 100 μCi of $Na_2{}^{51}CrO_4$ at 37° C. B cell lines were similarly pelleted and labeled with $^{51}Cr$. Labeled cells were washed twice with HBSS to remove unbound $^{51}Cr$ and the cells were then resuspended at $5 \times 10^4$/ml TCM. 100 μl of target cells were added to each assay well.

For peptide pulsing assays, 20 μl of individual HPLC fractions were added to wells containing $^{51}Cr$-labeled B cell target. The resulting peptide-target mixture was incubated for 1–2 hours at 37° C. to allow time for peptide charging of target cells. In those wells not receiving peptide, i.e., spontaneous release, experimental control, and maximal release wells, a 20 μl aliquot of TCM was used. 100 μl of TIL effector cells (5:1 effector-to-target ratio peptide-pulsing assays or various ratios from 20:1 to 5:1 for non-peptide pulsing assays) were added to assay wells and the contents of the 96 well plates were then incubated for 4 hours at 37° C. Spontaneous release wells received 100 μl TCM and maximum release wells received 100 μl of Triton X-100 (10% v/v in water). 100 μl of the resulting solution was harvested from each well and counted in a gamma-counter (LKB Pharmacia).

The results were reported in percent specific chromium release that was calculated as: % Specific Chromium Release=(Experimental cpm-Spontaneus cpm)/(Maximum cpm-Spontaneous cpm).

Spontaneous release was always less than 20% of the maximal release value. For some assays the assay results were reported in lytic units ($LU_{20}/10^7 EC$) based on 1 LU being equal to that number of TIL (EC (effector cells)) that were required to generate 20% specific lysis of the target.

The HLA-A2 status of all cell lines was assessed by indirect immunofluorescence assays as described above using the BB7.2 (anti-HLA-A2) monoclonal antibody and a fluorescein-labeled goat anti-mouse Ig (IgA+IgG+IgM) $F(ab')_2$ secondary reagent (Organon Teknika).

In the following example it is shown that treatment with peptide elution buffer according to the present invention diminishes melanoma class I expression and sensitivity to TIL.

EXAMPLE 9

$^{51}Cr$-labeled melanoma target cells (Mel 397 (HLA-A2⁻) and Mel 526 (HLA-A2⁺)) were treated with pH 3.3 isoosmotic, citrate-phosphate buffer for 1 minute, neutralized with TCM, and used in 4 hour cytotoxicity assays with TIL 1128 effector cells. Alternatively, the buffer treated cells were neutralized and allowed to regenerate their class I-peptide complexes for 18 hours at 37° C. and the sensitivity to TIL 1128 was assessed in 4 hour cytolytic assays. The results are shown below in Table 4.

TABLE 4

| Target Melanoma | HLA-A2 (+/−) | Acid Treatment (+/−) | Culture for 18 h post acid treatment (+/−) | TIL 1128 Lysis $LU_{20}/10^7$ EC |
|---|---|---|---|---|
| 526 | + | − | − | 168 |
|  | + | + | − | 8 |
|  | + | + | + | 152 |
| 397 | − | − | − | 14 |
|  | − | + | − | 4 |
|  | − | + | + | 12 |

As can be seen by the Table 4 results, acid treatment of the Mel 397 and Mel 526 target cells for 1 minute resulted in greater than 90–95% reduction of MHC class I molecule expression as monitored by the W6/32 (anti-class I monomorphic determinant), BB7.2 (anti-HLA-A2), or BBM-1 (anti-$β_2$-microglobin) MAb reagents and flow cytometry. As was to be expected, the level of class I complex denaturation rendered Mel 526 targets resistant to TIL 1128-mediated lysis in the 4 hour $^{51}Cr$-release assays. By comparison, Mel 397 (HLA-A2⁻) targets were not susceptible to TIL 1128 lysis under any conditions. Because the cells remained ≧90% viable after acid treatment, the targets were able to be recultured. Both class I expression (W6/32 reactivity) and sensitivity to T1L 1128 lysis returned to the control level by 18 hours in the Mel 526 targets, but not by 4 hours post-acid treatment, as demonstrated previously.

In the following example it is shown that the peptide buffer eluate resulting from treatment of melanoma target cells contains reactive peptide epitopes.

EXAMPLE 10

$10^8$ of each of Mel 397 (HLA-A2⁻), Mel 526 (HLA-A2⁻), and Mel 624 (HLA-A2⁺) cells were treated with iso-osmotic, pH 3.3 peptide elution buffer for 1 minute and the respective cell-free supernatants were collected. The individual supernatants were then desalted and concentrated on SepPak $C_{18}$ cartridges. The resulting peptides were then fractionated on Centricon 3 ultrafiltration devices in order to isolate peptides of molecular weight ≦3,000 Da. $10^6$ K4B cells (HLA-A2⁺) B target cells were then incubated with either TCM or the bulk peptides from the Mel 397, Mel 526, or Mel 624 cells in TCM plus 100 μCi of $^{51}Cr$ for 18 hours at 37° C. Mel 397, Mel 526, and Mel 624 target cells were also labeled for 1 hour with 100 μCi of $^{51}Cr$ at 37° C. The target cells were then washed to free unbound peptides and examined for sensitivity to TIL 1074 and TIL 1128 (HLA-A2 restricted melanoma-specific) -mediated lysis in 5 hour cytolytic assays. The results of these studies are shown in Table 5 below.

TABLE 5

| Target Cell | HLA-A2 (+/−) | 18 h incubation with peptides derived from: | TIL Reactivity TIL 1074 | ($LU_{20}/10^7$ EC) TIL 1128 |
|---|---|---|---|---|
| K4B | + | — | 12 | 4 |
| " | + | Mel 397 (A2⁻) | 21 | <4 |
| " | + | Mel 526 (A2⁺) | 88 | 75 |
| " | + | Mel 624 (A2⁺) | ND | 85 |
| Mel 397 | − | — | 10 | 6 |
| Mel 526 | + | — | 135 | ND |
| Mel 624 | + | — | ND | 85 |

ND = Not Done

As seen in Table 5, neither the TIL 1074 nor the TIL 1128 cells lysed the K4B control target cell line or the K4B target cells that were charged with peptides derived from the HLA-A2⁻ Mel 397 tumor cell line. The K4B cells that were pre-incubated with peptides derived from the HLA-A2⁺ melanoma targets (Mel 526 and Mel 624) however, were efficiently lysed by both TIL 1074 and TIL 1128 to a degree that was comparable to the parental Mel 526 and Mel 624 target cell lines. These findings support the hypothesis that TIL T cell epitopes were being eluted from HLA-A2 molecules that were expressed on the cell surface of melanoma cells by the pH 3.3 peptide elution buffer treatment.

In the following example the number and shared nature of HLA-A2-presented melanoma peptides were studied.

EXAMPLE 11

Figure 6A:
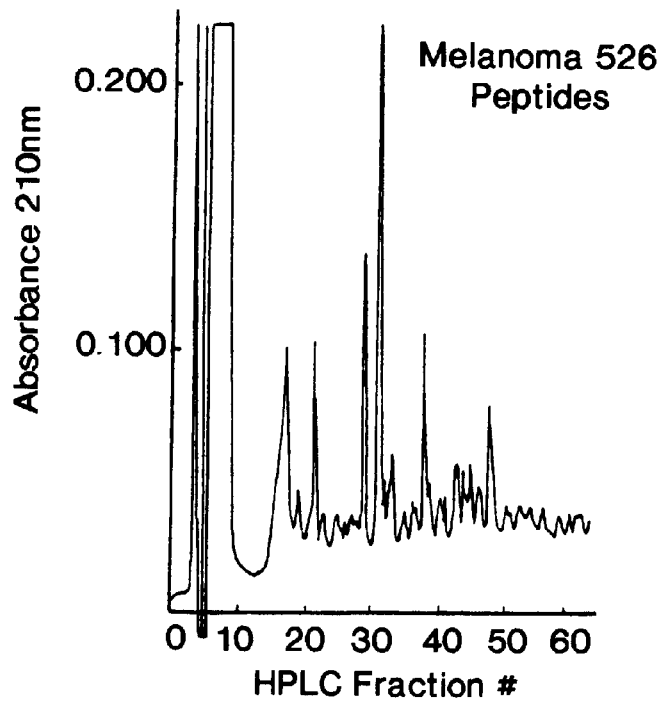
FIGS. 6A and 6B are RP-HPLC chromatograms of endogenously processed peptides that were eluted from Mel 526 (FIG. 6A) and Mel 624 (FIG. 6B) cells and monitored at 210 nm.
Figure 6B:
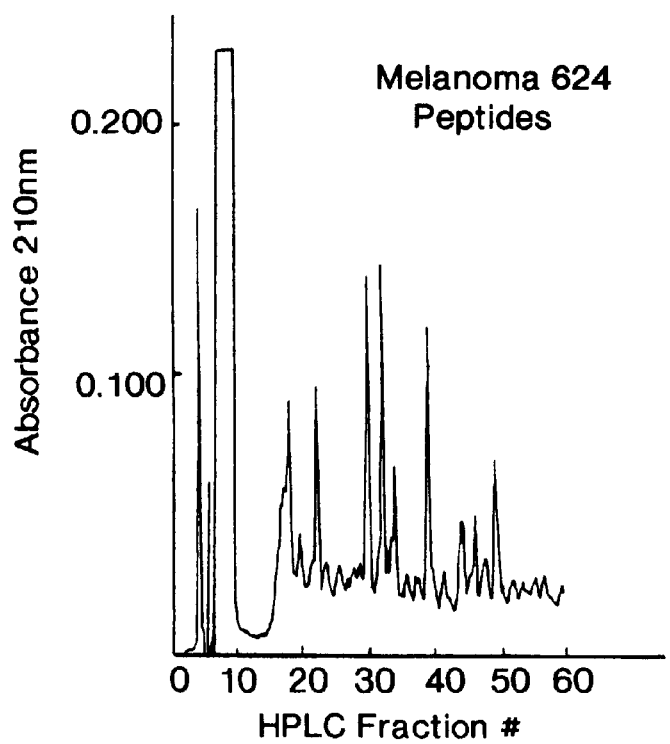

Peptides were eluted from 2×10$^8$ cells from the HLA-A⁺ Mel 526 and 624 cell lines by treatment with pH 3.3 iso-osmotic, citrate-phosphate buffer for 1 minute at 37° C. as described previously. The treatments were repeated daily allowing the tumor cells to regenerate the class I-peptide complexes overnight. The approximately 2×10$^{10}$ cell equivalents of each peptide was obtained after 4 days. The eluted peptides were subjected to SepPak C18 column chromatography and Centricon-3 ultrafiltration to select for peptides that were ≦3,000 Mr. Such peptides were then fractionated on RP-HPLC in a linear step gradient of 0%–35% acetonitrile (in water) monitored at 210 nm from water (containing 0.08% TFA) to 35% acetonitrile/64.93% water/0.07% TFA at a flow rate of 0.8 ml/minute. The results are shown in FIGS. 6A and 6B. Numerous peaks were identified based on absorbence at 210 nm for both cell lines.

The HPLC fractions from either Mel 526, Mel 624, or Mel 397 cells were then lyophilized to remove organic solvent, and resuspended in 200 μl of HBSS. 20 μl aliquots were used to pretreat 10$^4$ previously $^{51}$Cr-labeled, washed K4B B cell targets (HLA-A2⁺) in individual microwells of a 96-well U bottom assay plate and the solutions were incubated for 1 hour at 37° C. for peptide loading of HLA class I molecules. TIL 1074 or TIL 1128 effector cells (HLA-A2-restricted, melanoma-specific) were then added at an effector-to-target ratio 5:1. Five hour cytotoxicity assays were then performed.

Figures 1, 7A:
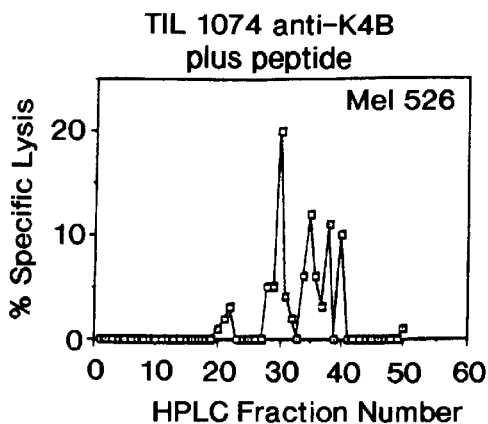
FIGS. 7A and 7B are graphs showing the presence or absence of individual T cell epitopes that were eluted from three melanoma cell lines and then recognized by TIL 1074 (FIG. 7A) or TIL 1128 (FIG. 7B) mediated cytolysis of K4B target cells. The percent specific lysis of target cells is shown as a function of the individual HPLC fractions eluted from Mel 526, Mel 624, and Mel 397 human melanoma cell lines according to the present invention and loaded onto the target cells.
Figures 1, 7B:
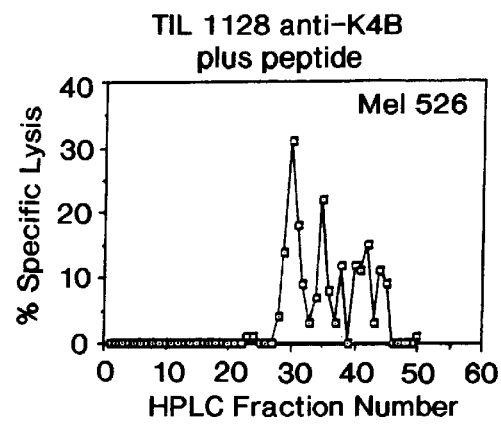
Figures 2, 7A:
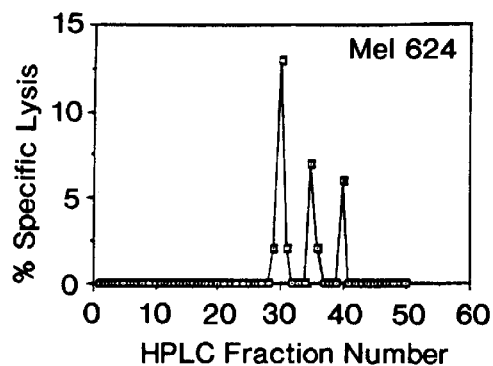
Figures 2, 7B:
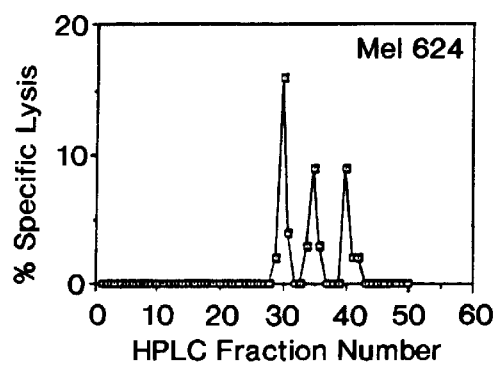
Figures 3, 7A:
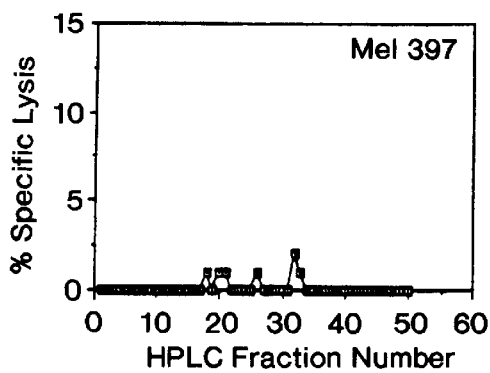
Figures 3, 7B:
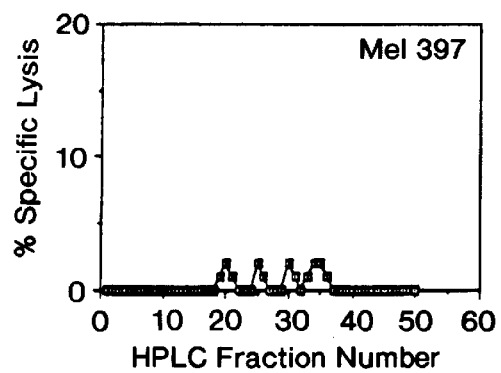

The results which are shown in FIGS. 7A and 7B show there are six individual T cell epitopes (P1–P6) that were eluted from Mel 526 cells and which were recognized by TIL 1128 in TIL 1128-mediated cytolysis of K4B target cells in the following HPLC fractions: P1 (fraction 30); P2 (fraction 35); P3 (fraction 38); P4 (fraction 40); P5 (fraction 42); and P6 (fraction 44). Three of these TIL 1128-reactive peptides (P1, P2, P4) also appeared to be present in Mel 624 peptide preparations since Mel 624 HPLC fraction numbers 30, 35, and 40 contained peptides recognized by TIL 1128. Mel 397 (HLA-A2-) HPLC fractions did not appear to contain any of the peptides significantly recognized by TIL 1128. In similar assays using TIL 1074, the TIL appeared to recognize P1–P4 derived from Mel 526 (but not P5 or P6); P1, P2, and P4 that were derived from Mel 624; but no HPLC fractions derived from Mel 397. No TIL reactive peptides could be demonstrated in HPLC fractions derived from acid extracted HLA-A2⁺ B cell lines (data not shown). HLA-A2⁺ B cells were not recognized or lysed by either TIL 1074 or TIL 1128 peptides derived from these cells and peptides derived from these cells are not recognized by these TIL.

In the following example it is shown that P1, P2, and P4 represent "shared" melanoma determinants.

EXAMPLE 12

In this example an additional HLA-A2 restricted (oligoclonal) TIL (E92-19 was included along with two additional HLA-A2⁺ melanoma target cell lines, Mel 397.A2 (an HLA-A2⁺ transfectant of Mel 397 available from Yataka Kawakami, NIH and described in Kawatami, Y., et al., *J. Immunol.* 148:638 (1992), the disclosure of which is incorporated herein by reference), and WM35 a gift of Dr. M. Hertlyn, Wistar and generally available. As shown below in Table 6 HPLC fractions derived from Mel 526 buffer extracts that contained TIL 1128 reactive epitopes (P1–P6) were incubated with 10$^4$ K4B (HLA-A2⁺) target cells that were previously incubated with $^{51}$Cr for 1 hour at 37° C. These peptide-pulsed targets were then used in 5 hour cytolytic assays with TIL 1074, TIL 1128, and TIL E92-19 effector cells. The results shown below in Table 6 were reported as (+) if TIL lysis of peptide-pulsed targets exceeded TIL lysis of TCM (control) treated K4B cells by more than 2 standard deviations. A pattern of TIL reactivity to P1–P6 was established as seen below.

TABLE 6

| | Bioactive HPLC Peak Fractions | | | | | |
|---|---|---|---|---|---|---|
| TIL | P1 (25) | P2 (30) | P3 (35) | P4 (40) | P5 (42) | P6 (44) |
| 1074 | + | + | + | + | − | − |
| 1128 | + | + | + | + | + | + |
| E92-19 | + | + | − | + | + | + |

As seen above, 3 out of 3 HLA-A2 restricted melanoma-specific TIL cell lines recognized P1, P2, and P4. TIL 1074 and TIL 1128, but not TIL 392-19, recognized P3. Only TIL 1128 recognized P5. TIL 1128 and TIL 392-19 but not TIL 1074, recognized P6.

In the following example a heterogeneous response to P1–P6 to oligoclonal TIL populations was exhibited.

EXAMPLE 13

Peptides were extracted from 10$^8$ cells of each of the following melanoma cell lines by iso-osmotic, pH 3.3 peptide elution buffer treatment: Mel 397, Mel 397.A2, Mel 526, Mel 624, and WM35. After extraction, the peptides from each cell line were individually subjected to fractionation on reverse-phase HPLC as described previously. The fractionated peptides were then lyophilized and reconstituted in HBSS as also described above. The individual fractions from the various cell lines were then pulsed onto $^{51}$Cr-labeled K4B targets for 1 hour at 30° C. TIL 1128 which were shown to recognize P1–P6 in Example 11 were then used as effector cells against these peptide-pulsed targets in 5 hour chromium release assays. In the results shown below in Table 6, peptides in HPLC fractions 30 (P1), 35 (P2), 38 (P3), 40 (P4), 42 (P5) or 44 (P6) that were capable of inducing K4B lysis greater than 2 standard deviations above the TCM control treated K4B target cells were denoted as (+)

TABLE 7

| | Expression of TIL 1128 reactive: | | | | | |
|---|---|---|---|---|---|---|
| Melanoma Line | HLA-A2 (+/) | P1 | P2 | P3 | P4 | P5 | P6 |
| Mel 397 | − | − | − | − | − | − | − |
| Mel 397.A2 | + | + | + | − | + | − | − |
| Mel 526 | + | + | + | + | + | + | + |
| Mel 624 | + | + | + | − | + | − | − |
| WM 35 | + | + | + | − | + | − | + |

These results show a heterogeneity at both the level of the melanoma cell line (peptide producer) and the oligoclonal TIL responder. Thus up to 4 TIL "clonal reactivity patterns" were determined. Pattern 1 recognized P1, P2, and P4. Pattern 2 recognized P3 only (present in TIL 1074 and TIL 1128, but not TIL E92-19.) Pattern 3 recognized P5 only (present in TIL 1128 only). Pattern 4 recognized P6 (present in TIL 1128 and TIL 392-19, but not TIL 1074). The pattern of P1–P6 expression by individual melanomas suggest that P1, P2, and P4 are coordinately expressed by all four HLA-A2+ melanoma cell lines examined, including the HLA-A2+ transfectant Mel 397.A2. When this observation is combined with the "clonotype 1" pattern of reactivity in 3 out of 3 oligoclonal TIL cell lines shown in Table 7, it is strongly indicated that P1, P2, and P4 represent shared HLA-A2-presented melanoma determinants. P3, P5 and P6 displayed more heterogeneous expression whereas P3 and P5 were expressed only by Mel 526. P6 was expressed by Mel 526 and WM35, but not Mel 397.A2 or Mel 624 cell lines.

These results indicate that P1, P2, and P4 may potentially be developed for vaccines as they appear to constitute immunodominant, shared melanoma peptides.

In the next example P1–P6 were analyzed for their ability to be presented in the context of diverse class I allotypes.

EXAMPLE 14

Figure 8A:
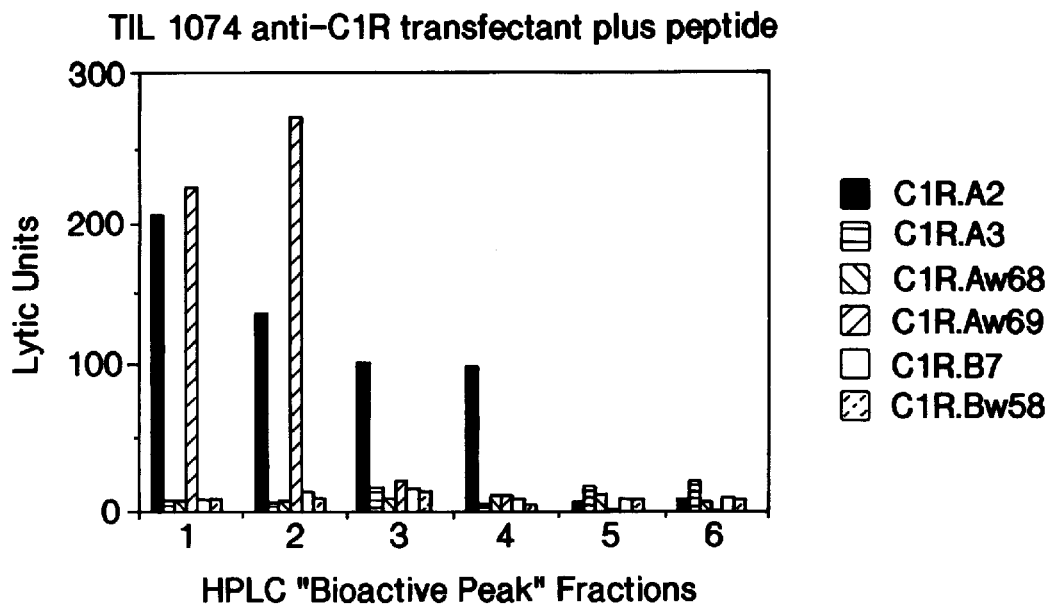
FIGS. 8A and 8B are graphs showing the ability of diverse class I allotypes (HLA-A2, -A3, -Aw68, -Aw69, -B7 and -Bw58) to present the six HPLC bioactive peak fractions (P1–P6) that were eluted from Mel 526 as measured by TIL 1074 (FIG. 8A) or TIL 1128 (FIG. 8B) mediated cytolysis of targets (C1R transfectants expressing various class I molecules (C1R.A2, C1R.A3, C1R.Aw68, C1R.A269, C1R.B7 and C1R.Bw58)). The lysis of each type of target cell is shown in lytic units for the peptides of each of the six HPLC fractions that were loaded onto each of the target cell types.
Figure 8B:
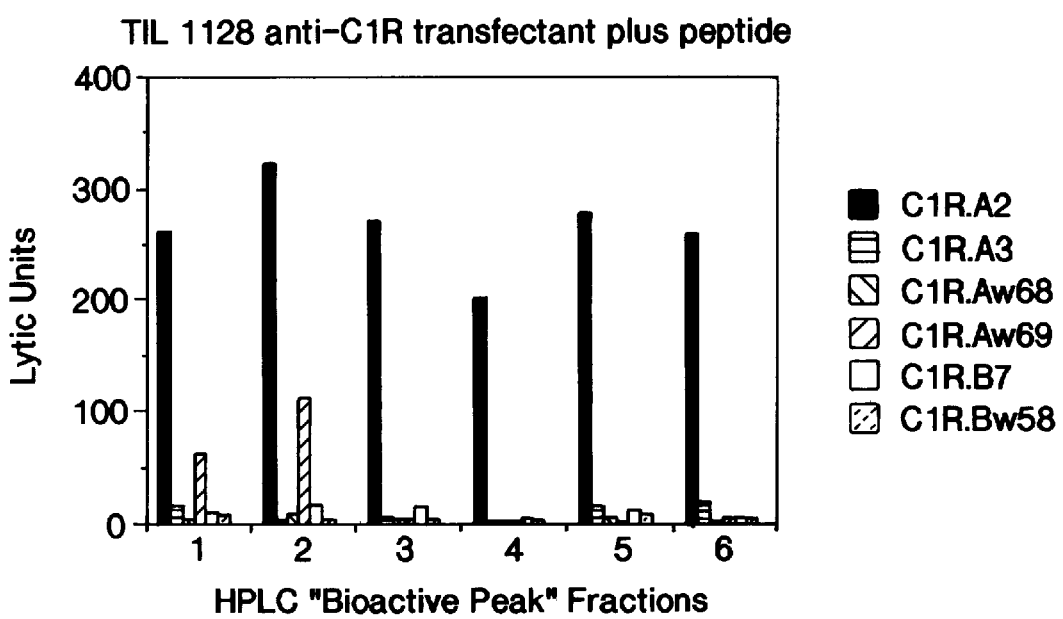

The HPLC fractions that were derived from Mel 526 that contained the six HPLC bioactive peak fractions P1–P6 (fractions 25, 30, 35, 40, 42, and 44, respectively) were pulsed at 37° C. for 1 hour onto $10^4$ $^{51}$Cr-labeled C1R transfectants that expressed essentially homogeneous populations of HLA-A2, -A3, -Aw68, -Aw69, -B7, or -Bw58 class I trans gene products. The peptide-pulsed target cells were then examined for sensitivity to TIL 1074- or TIL 1128-mediated cytolysis in 5 hour cytolytic assays. The results are shown in FIGS. 8A and 8B as Lytic Units ($Lu_{20}/10^7$ EC).

It is seen that both P1 and P2 were efficiently presented by HLA-A2 (expressed by C1R.A2 targets) and HLA-Aw69 (expressed by C1R.Aw69 targets) to both TIL 1074 and TIL 1128. P3 and P4 were presented only by HLA-A2 cells to both TIL 1074 and TIL 1128. P5 and P6 were recognized by TIL 1128, but only in the context of HLA-A2. Other HLA class I molecules, HLA-A3 (expressed by C1R.A3), HLA-Aw68 (expressed by C1R.AW68), HLA-B7 (expressed by C1R.B7), and HLA-Bw58 (expressed by C1R.Bw58, were ineffective at presenting P1–P6 to either TIL line.

It has been shown in the art that synthetic peptide sequences corresponding to class I-presented, CD8+ T cell-recognized peptides (T cell epitopes) are capable of both priming and restimulating CD8+ cytotoxic T cells in vitro. See, for example, Wolfel, T., et al., *Immunogenet.* 26:178 (1987), the disclosure of which is incorporated herein by reference. Further, the length of peptide has been shown to be critical in determining the immunogenic potential of peptides in vitro and in vivo. Peptides 8 to 12 amino acids in length have been identified as the biologically relevant CD8+ T cell recognized species and have been shown in the art to represent the optimal immunogen. See, for example, Rotzschke, O., et al., *Nature* 348:252 (1990), the disclosure of which is incorporated herein by reference.

In view of the above findings that melanomaspecific cytotoxic T lymphocytes define a minimum of six Class I-presented peptide epitopes common to most HLA-A2+ melanomas, the following examples were carried out to further identify melanoma-associated epitopes that are presented by the HLA-A2 allele to T cells.

III. Methods—Identification of Melanoma T Cell Epitopes
Cell Lines

Two melanoma cell lines were used throughout this study. Mel 624 (HLA-A2, -A3, -B7, -B14; -Cw7; was obtained as identified above and Mel 9742 (HLA-A2; -A24; -B13, -B18; -Cw6, -Cw7; was obtained from the Instituto Nazionale Tumori, Milan, Italy), a gift, and available on request. Both cell lines were cultured in TCM consisting of RPMI-1640 media that was supplemented with 10% heat-inactivated fetal bovine serum, 100 IU/ml penicillin, and 100 µg/ml streptomycin (all reagents from Gibco BRL, Gaithersburg, Md.) and were otherwise cultured as described in Example 1.

The following CTL lines and clones that were derived from five different melanoma patients were also used in this study. The CTL clone A83 (autologous to Mel 9742) (kindly provided by Dr. G. Parmiani of Instituto Nazionale Tumori, Milan, Italy and available upon request) recognizes a common melanoma antigen and is restricted by HLA-A2 as reported by Anichini, A., et al., *J. Exp. Med.* 177:989 (1993), the disclosure of which is incorporated herein by reference. The tumor infiltrating (TIL) 1235 line and TIL 501.A42 clone were kindly provided by Dr. Y. Kawakami (National Institutes of Health, Bethesda, Md.), and available upon request. TILs 5403 and 6970 were isolated from metastatic melanoma lesions of HLA-A2+ patients as described by Whiteside, T. L., et al., *J. Immunol. Methods* 90:221 (1986), the disclosure of which is incorporated herein by reference. TILs 5403 and 6970 were cultured for 7 days in the presence of autologous tumor and were used directly as effector cells in cytotoxicity experiments. All of the TIL lines and clones were cultured in AIM-V media (Gibco BRL) that was supplemented with 10% heat-inactivated human AB serum (Gibco), and 300 IU/ml rhIL-2 (Cetus Corp., Emeryville, Calif.).

Acid Elution of MHC Class 1-Presented Melanoma Peptides (T Cell Epitopes)

Acid elution of, and reverse-phase high performance liquid chromatography (RP-HPLC) resolution of, melanoma peptides was performed as described above in Examples 1 and 6. Individual HPLC fractions that were obtained were lyophilized and reconstituted in 200 µl of Hank's buffered saline (Gibco BRL) and stored at −20° C. for use in the cytolytic assays. Alternatively, for mass spectrometric analyses, the eluted and fractionated peptides were lyophilized and reconstituted in 50 µl of 50% water and were then stored at −70° C. until they were used.

Reconstitution of T Cell Epitopes In peptide-pulsing assays, 10 µl of peptides (in buffer) were added to microculture wells containing $10^4$ $^{51}$Cr-labeled T2 target cells (T2 cells were kindly provided by Peter Cresswell, Yale University, and are available upon request), 0.2 µg human $\beta_2$-microglobulin ($\beta_2$-m; Sigma Chemical Co., St. Louis, Mo.), and 0.2 µg MA2.1 (anti-HLA-A2.1 available from American Type Culture Collection, Rockville, Md. and described in McMichael, A. J., et al., *Hum. Immunol.* 1:121 (1980) the disclosure of which is incorporated herein by reference) monoclonal antibody in a total of 125 µl. Peptide loading was facilitated by the presence of the $\beta_2$-m and MA2.1 reagents as described by Zeh, H. J., et al., Hum. Immunol. 39:79 (1994), the disclosure of which is incorporated herein by reference. The cells were then incubated for 2 hours at room temperature. Effector T cells were then added at a 10:1 effector-to-target cell ratio (unless otherwise stated) and standard 4 hour cytolytic assays were performed as described in Example 5.

HLA-A2 Stabilization Assay

Various concentrations of synthetic peptides as noted below were incubated for 18 hours at room temperature with $10^6$ T2 cells (Salter, R. D., et al., *Immunogenetics* 21:235 (1985), the disclosure of which is incorporated herein by reference) 1 μg $β_2$-m, and 2 μg MA2.1 monoclonal antibody. The cells were then washed twice with buffered saline and stained with FITC-conjugated F(ab')$_2$ goat anti-mouse Ig (Organon Teknika, Durham, N.C.) for 30 minutes at 4° C. After two additional washes with buffered saline, the cells then were fixed with 4% formalin (Fisher Scientific Co., Pittsburgh, Pa.). The assays were monitored by flow cytometry that was performed on a FACScan flow cytometer (Becton Dickinson, Mountain View, Calif.) as described above with reactivity expressed in mean fluorescence channel (MFC) units. The results are reported as the percentage of increase over control of MA2.1 MFC number reactivity. Controls are represented by T2 cells cultured with $β_2$-m and MA2.1 monoclonal antibody, in the absence of synthetic peptide.

Mass Spectrometric Analysis

Mel 9742 HPLC fractions 47 and 48, obtained as described above, were pooled, lyophilized, and then reconstituted in 50 μl of 50% acetonitrile, 50% double distilled $H_2O$, and stored at −70° C. A 10 μl aliquot of this material was then introduced into an API III tandem mass spectrometer (PE-Sciex, Ontario, Canada) via the articulated ionspray interface. The sprayer needle was held at 4,500 V with a coaxial sheath of nebulizing gas (compressed air) flow. Profile mass spectrums were obtained for peptide samples by scanning the first quadrupole from mass-to-charge (m/z) 500 to 1,600 in 3.37 seconds. The final spectrum was averaged from 10 scans. A mass spectra/mass spectra (MS/MS) product ion spectrum was obtained for the peptide species exhibiting m/z=941, hereinafter referred to as p939, by scanning the fragment ions resulting from collision with argon gas. The sequence was assigned as XXTVXXGVX (SEQ ID NOS: 6–37), where X=isoleucine or leucine, each with residue mass of 113.

Synthetic Peptides

The peptides used for these studies were synthesized using FMOC chemistry by the Peptide Synthesis Facility (Shared Resource) of the Pittsburgh Cancer Institute. Each synthesized peptide was purified to >95% homogeneity by reverse-phase (RP) HPLC. The identity of each peptide was confirmed by MS/MS. The following peptides were synthesized: p939/MART-1 32–40:ILTVILGVL (Ile-Leu-Thr-Val-Ile-Leu-Gly-Val-Leu) (SEQ ID NO: 38); gp100 280–288:YLEPGPVTA (Tyr-Leu-Glu-Pro-Gly-Pro-Val-Thr-Ala) (SEQ ID NO: 39) as described by Cox, A. L., et al., *Science (Wash. DC)* 264:716 (1994), the disclosure of which is incorporated herein by reference; HIV-nef 73–82:QVPL-RPMTYK (Gln-Val-Pro-Leu-Arg-Pro-Met-Thr-Tyr-Lys) (SEQ ID NO: 40) as described by Culmann, B. E., et al., *Eur. J. Immunol.* 19:2383 (1989), the disclosure of which is incorporated herein by reference; infleunza A matrix, Flu M1 58–66:GILGFVFTL (Gly-Ile-Leu-Gly-Phe-Val-Phe-Thr-Leu) (residues of 2–10 SEQ ID NO: 1); p53 186–196:DGLAPPQHLIR (Asp-Gly-Leu-Ala-Pro-Pro-Gln-His-Leu-Ile-Arg) (SEQ ID NO: 41) as described by Zeh, H. J., et al., *Hum. Immunol.* 39:79 (1994), the disclosure of which is incorporated herein by reference; and p53 264–272:LLGRNSFEV (Leu-LeuGly-Arg-Asn-Ser-Phe-Glu-Val) (SEQ ID NO: 42) also described by Zeh, H. J., et al.

In the following example, the specific recognition of HLA-A2-presented melanoma peptides by CTL Clone A83 is shown.

EXAMPLE 15

Figures 1, 9A:
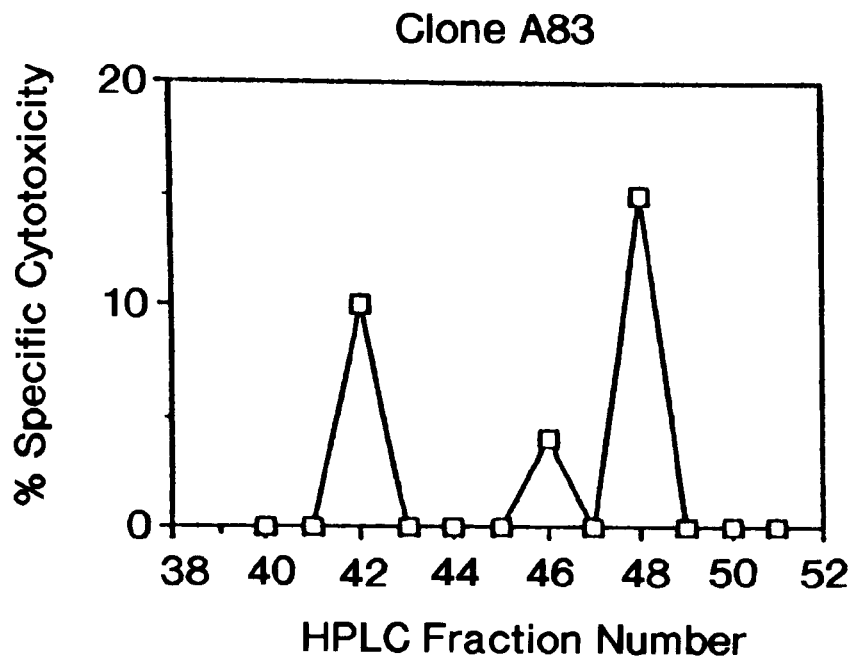
FIGS. 9A–9C are graphs showing the presence or absence of individual T cell epitopes that were eluted from two melanoma cell lines and then recognized by Clone A83 (FIG. 9A); TIL 1235 (FIG. 9B); or Clone A42 (FIG. 4C)— mediated cytolysis of T2 target cells. The percent of specific cytotoxicity is shown as a function of the individual HPLC fractions eluted from Mel 624 (top panels) or Mel 9742 (bottom panels) human melanoma cell lines according to the present invention.
Figures 2, 9A:
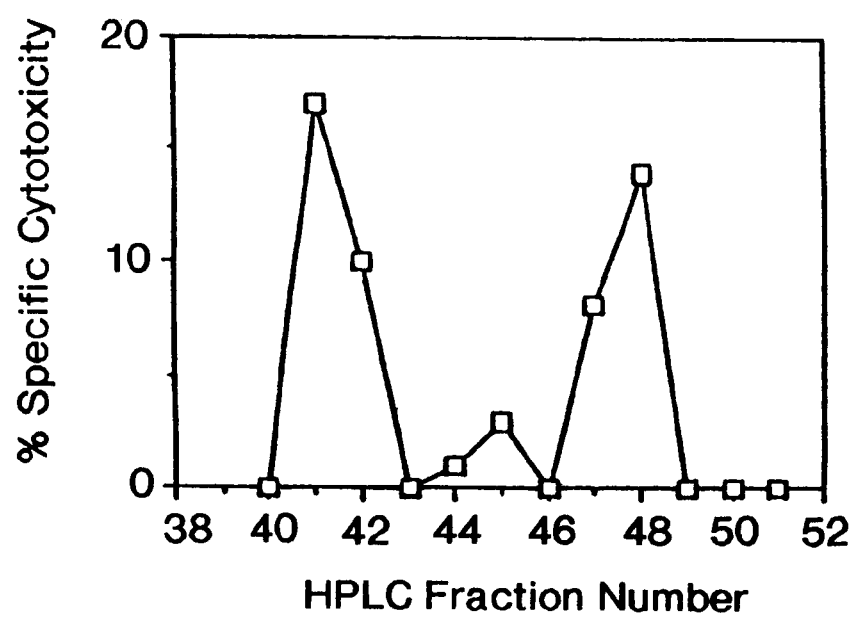
Figures 1, 9B:
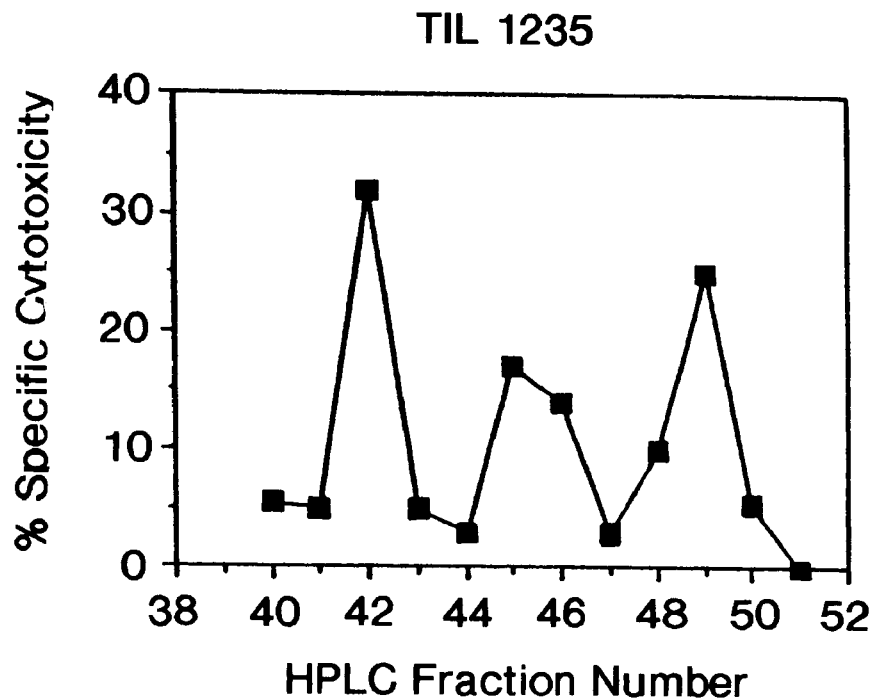
Figures 2, 9B:
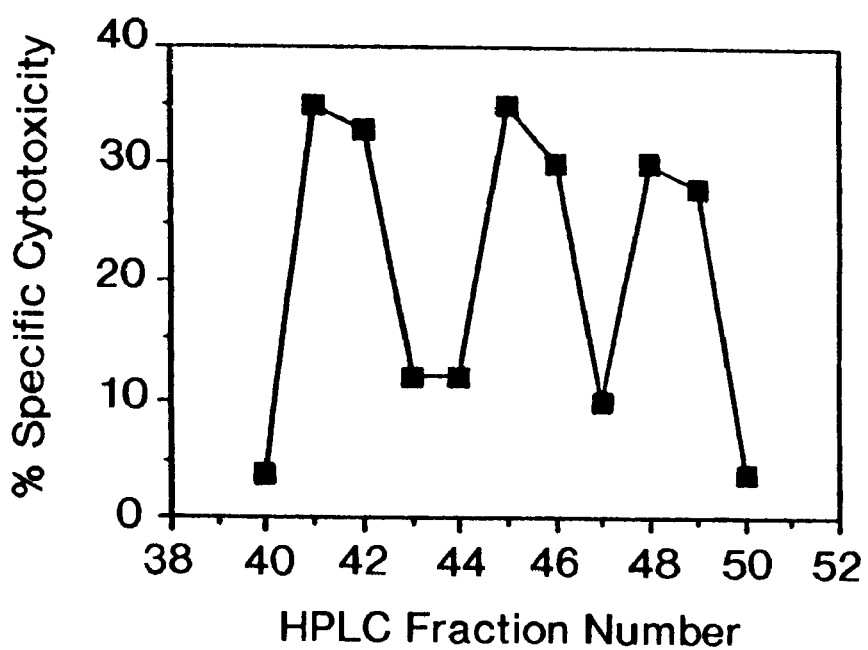
Figures 1, 9C:
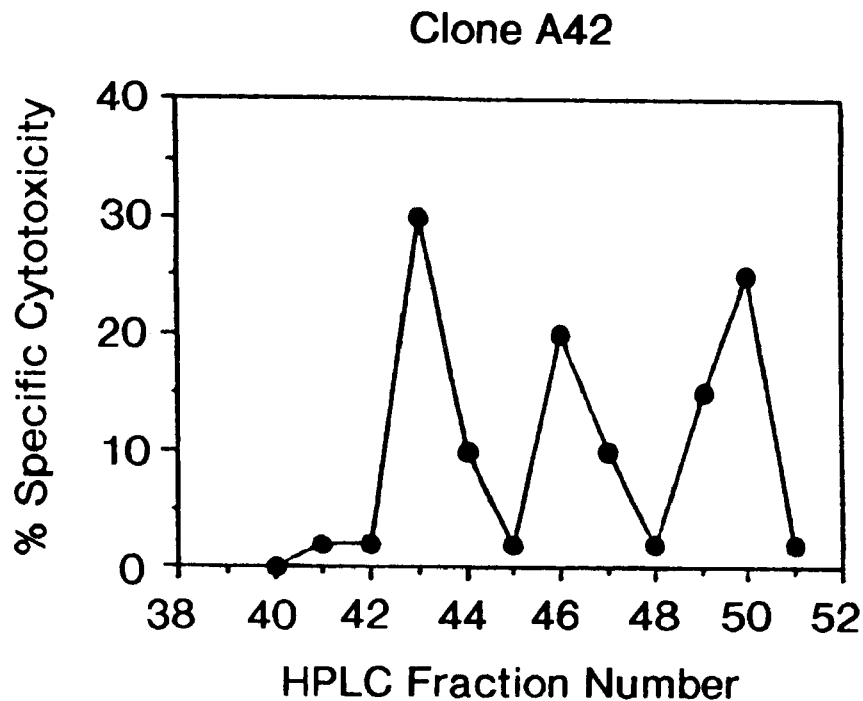
Figures 2, 9C:
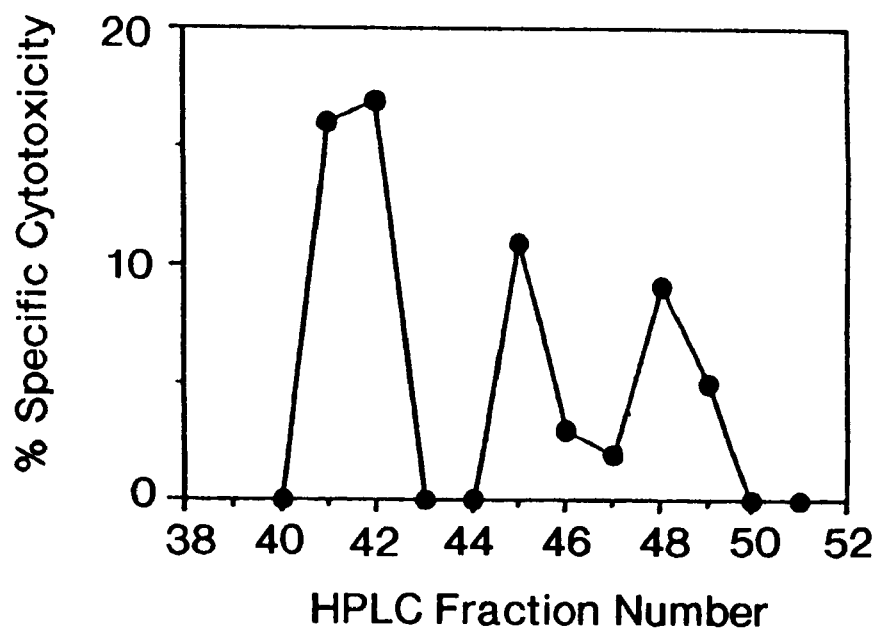

Melanoma 9742 (Mel 9742) and melanoma 624 (Mel 624) cells were treated as in Example 1 with peptide elution buffer (iso-osmotic, citrate-phosphate buffer at ph 3.3). Peptides were extracted from approximately $5×10^9$ cell equivalents of each cell type. Specifically, 3 sequential daily treatments were used to obtain each of the particular peptides in this case with the cells being allowed to regenerate their class I-peptide complexes between peptide elution buffer treatments. These peptides were then resolved by RP-HPLC as described above. The respective peptides were lyophilized and each fraction was then reconstituted in 200 μl of buffered saline. 10 μl aliquots of the individual fractions were then pulsed onto the HL-A2$^+$ T2 cell line that had been labeled with $^{51}$Cr, in the presence of human $β_2$-m and the anti-HLA-A2 monoclonal antibody MA2.1. CTL were then added at an effector-totarget cell ratio of 2:1 for Clone A83 or 10:1 for TIL 1235 and Clone A42 and standard 4-hour cytotoxicity assays were then carried out. The results of these assays are shown in FIGS. 9A–9C with % specific cytotoxicity of the CTL shown as a function of the RP-HPLC fractions of Mel 624 (top panels) and Mel 9742 (bottom panels)-derived peptides. HPLC fractions 1–38 pulsed onto the T2 cell line were not recognized by any of the CTL.

With respect to CTL Clone A83, three of the total of six bioactive peaks were identified for autologous Mel 9742 peptides, resolving in HPLC fractions 42–43, 45, and 47–48 as shown in FIG. 9A, bottom panel. A similar pattern of bioactive peaks was identified for allogeneic HLA-A2$^+$ Mel 624 fractionated peptides as also seen in FIG. 9A, top panel. Peak 1 (HPLC fraction 42–43) and peak 3 (HPLC fractions 47–48) exhibited comparable efficacy in sensitizing the T2 target cell to lysis by CTL clone A83, with peak 2 (HPLC fraction 45) displaying a somewhat lesser capacity to do so.

HLA-A2 restricted, melanoma-specific TIL 1235 (FIG. 9B) and CTL clone A42 (FIG. 9C) also recognized these same A83-identified bioactive peaks as detected by cytolysis of T2 peptide-pulsed target cells, with peak 2 reactivity approximating that of peaks 1 and 3.

Thus, the foregoing shows that these melanoma TIL lines (Lines 1235 and 6970) and clones (Clones A83 and A42) coordinately recognize three predominant T cell epitopes as resolved by RP-HPLC. In the following examples, one of these three naturally processed melanoma peptides/T cell epitopes was identified.

EXAMPLE 16

Figure 10A:
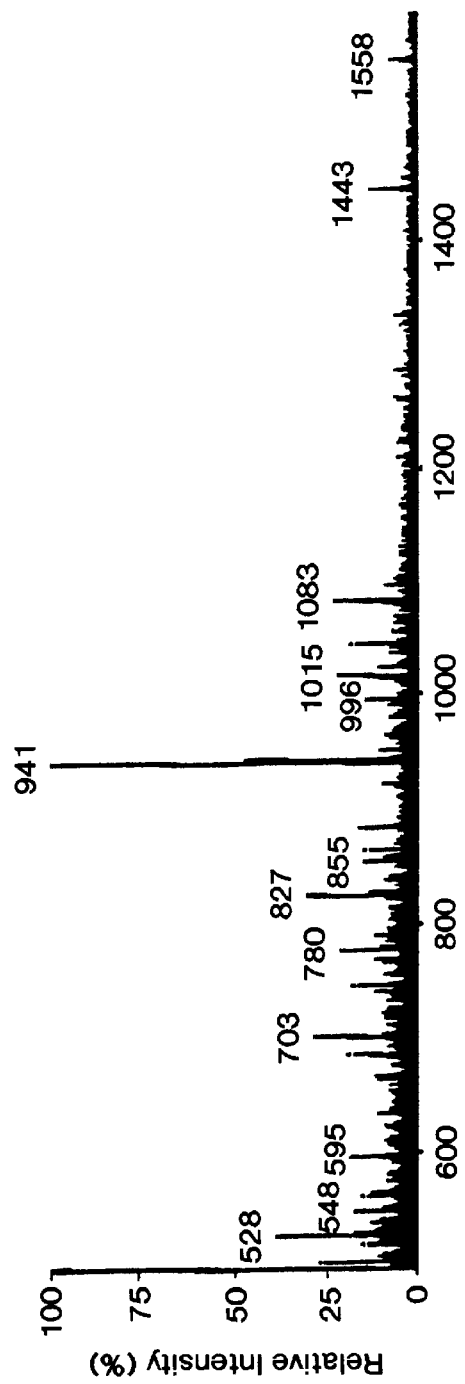
FIGS. 10A and 10B are mass spectra of HPLC peptide fractions 47 and 48 obtained from Mel 9742.
Figure 10B:
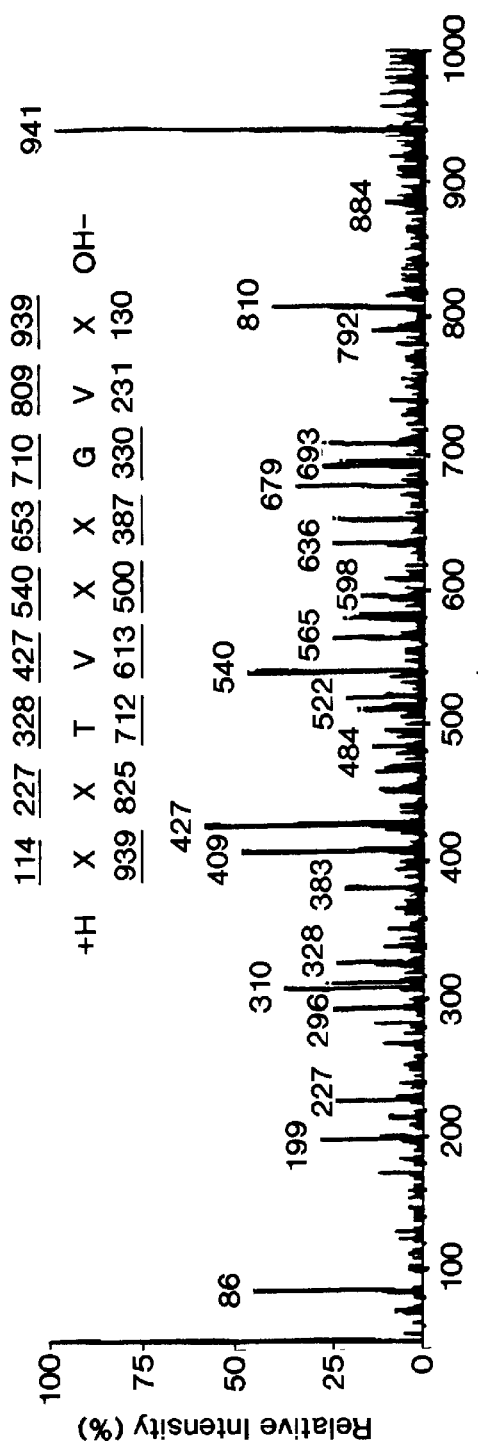

Mel 9742 HPLC fractions 47 and 48 (peak 3 shown in FIGS. 9A–9C, bottom panels) were pooled and analyzed using tandem mass spectroscopy. 10 μl of fractionated material, corresponding to 20% of the pooled fractions acid eluted from $5×10^9$ Mel 9742 cells, were injected into the triple quadrupole mass spectrometers electrospray ionizing source as described above The summation of mass spectra for peptides with m/z=500–1,600 is shown in FIG. 10A. As can be seen, at least 39 different peptides were detected, with one peptide (m/z=941) representing the predominant species. Collision-induced dissociation (CID) was performed on the peptide where m/z=941 (p939) which yielded the daughter ion spectrum shown in FIG. 10B. The spectra was interpreted as defining a nine-amino acid peptide of $M_r$=939 with the sequence XXTVXXGVX (SEQ ID NOS: 6–37), where X=isoleucine or leucine (single letter amino acid designations). Since isoleucine and leucine exhibit identical masses ($M_r$=113), 32 potential variants of this peptide sequence are possible. The ultimately deduced and biologically relevant peptide p939 appears to derive from a recently cloned melanoma-associated gene Melan A according to the results of a search of the GenBank database that yielded a complete homology for one of these sequences, ILTVILGVL (Ile-Leu-Thr-Val-Ile-Leu-Gly-val-Leu) (SEQ ID NO: 38). The complete Melan-A gene (accession number HSU06654) also known as MART-1, is described by Kawakami, Y., et al, *Proc. Nat. Acad. Sci. USA* 91:3515 (1994), the disclosure of which is incorporated herein by reference.

In the following example the binding affinity of p939 to HLA-A2 was determined.

EXAMPLE 17

The p939 deduced sequence ILTVILGVL (SEQ ID NO: 38) was synthesized and eluted in HPLC fractions 48/49, approximating the naturally processed bioactive form of p939 that was eluted from Mel 9742 as described above in the section on HLA-A2 stabilization assay. This peptide was then analyzed for its ability to bind to HLA-A2 using an HLA-A2-specific stabilization assay implementing the T2 cell line, as described by Zeh, H. J., et al., *Hum. Immunol.* 39:79 (1994) and Nijman, H. W., et al., *Eur. J. Immunol.* 23:1215 (1993), the disclosures of which are incorporated herein by reference. The T2 cell line exhibits severely depressed cell surface class I expression resulting from a genetic lesion affecting peptide transport into the endoplasmic reticulum, as described by Salter, R. D., et al., *Immunogenetics* 21:235 (1985), the disclosure of which is incorporated herein by reference. T2 expression of class I molecules, in particular HLA-A2, at the cell surface can be enhanced by incubation of T2 cells at a reduced temperature in the presence of exogenous $\beta_2$-m and peptides that are capable of binding to the HLA-A2 allele as reported by Zeh, H. J., et al., Boyd, L. F., et al, *Proc. Natl. Acad. Sci. USA* 89:2242 (1992) and Bodmer, H. G., et al., *Nature (Land.)* 342:443 (1989), the disclosures of which are incorporated herein by reference.

Figure 11:
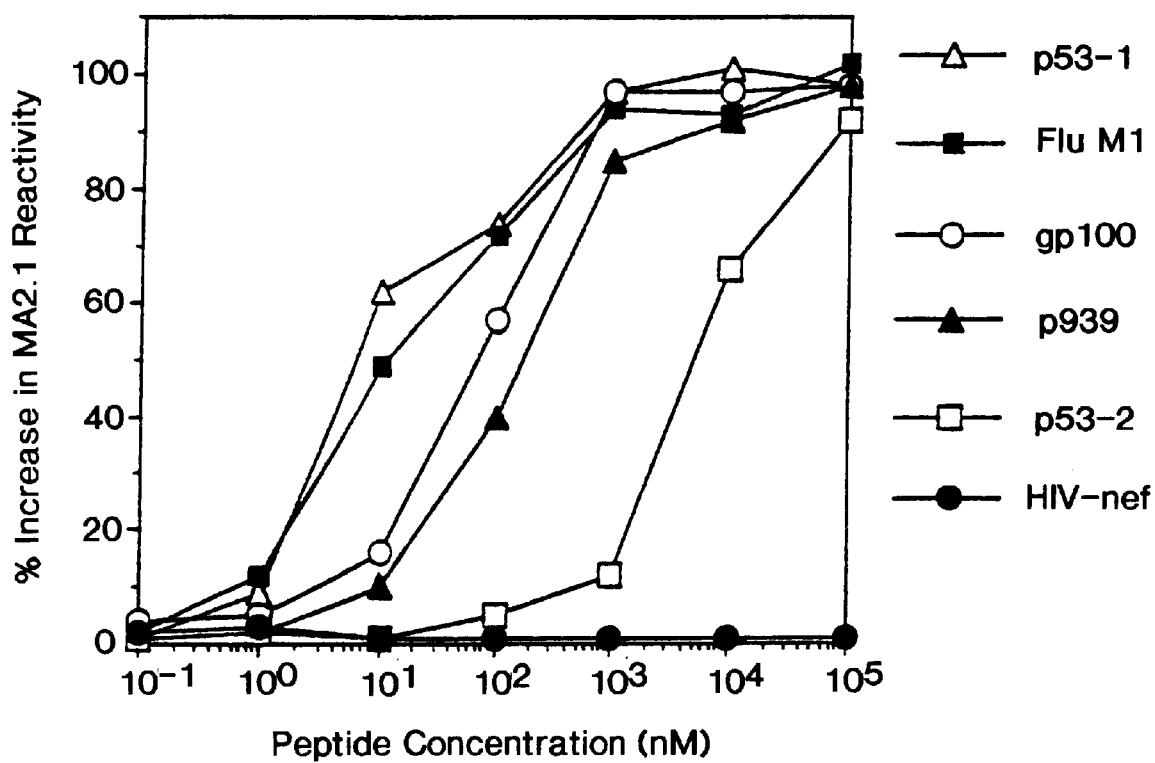
FIG. 11 is a graph showing the binding of peptide p939 to HLA-A2. HLA-A2 expression on the T2 cell line in the presence of increasing concentrations of various exogenous synthetic peptides including p939 was evaluated using MAb 2.1 (anti-HLA-A2 monoclonal antibody) in indirect immunoflourescent assays monitored by flow cytometry. Δ=p53-1; ■=Flu M1; ○=gp100; ▲=p939; □=p53-2; and ●=HIV-nef.
Figure 12A:
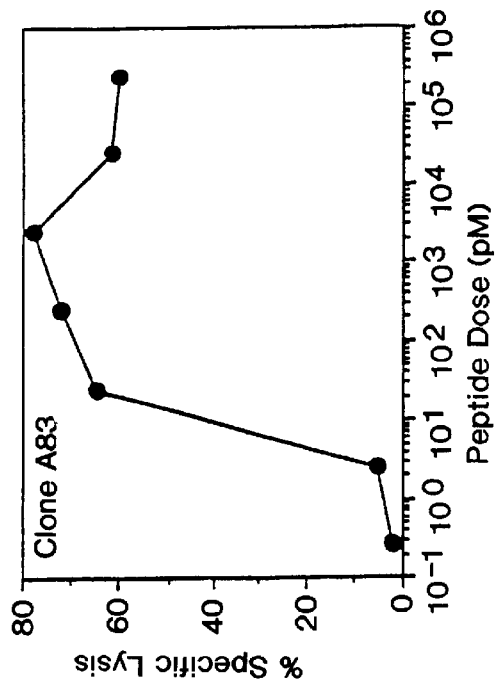
FIGS. 12A–12D show epitope reconstitution with peptide p939. Melanoma-specific CTL: cultured TIL 1235 (FIG. 12A); clone A83 (FIG. 12B); clone A42 (FIG. 12C); and fresh TIL 6970 (FIG. 12D) were assayed in standard cytotoxicity assays against $^{51}$Cr-labeled T2 cells pulsed with p939 at the indicated concentrations.
Figure 12B:
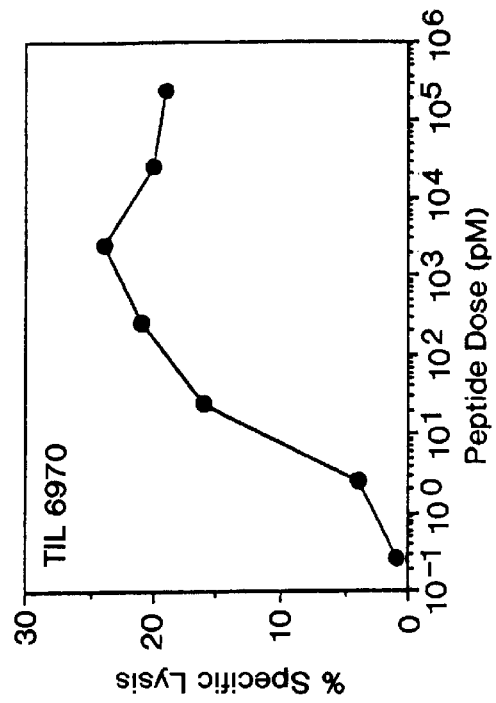
Figure 12C:
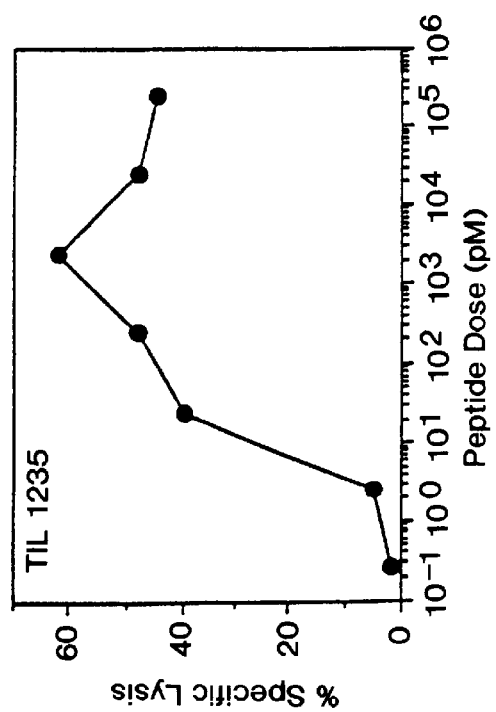
Figure 12D:
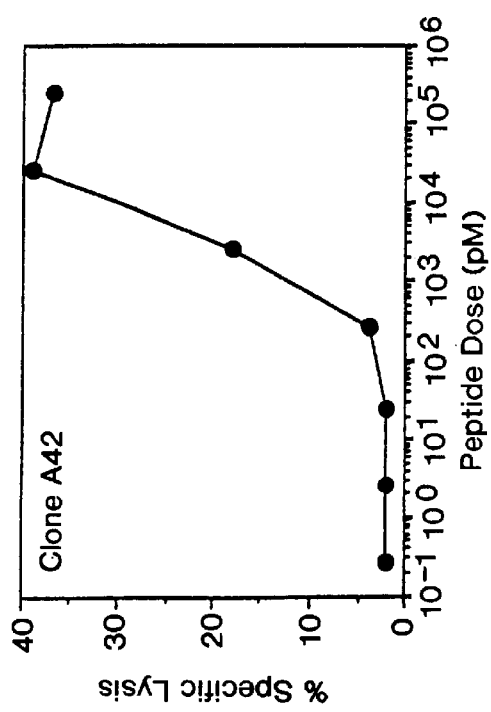

A panel of synthetic peptides, including p939, (p53-1; Flu M1; gp100; p939; p53-2; and NIV-nef) was incubated with the T2 cell line at room temperature (23° C.) for 18 hours and their capacity to stabilize HLA-A2 expression on the cell surface of T2 cells was evaluated using the MA2.1 (anti-HLA-A2 monoclonal antibody) in indirect immunofluorescence assays monitored by flow cytometry as described above (stabilization assay). Those peptides binding to HLA-A2 yielded an elevated reactivity with the MA2.1 (anti-HLA-A2) monoclonal antibody compared with non-peptide-treated or irrelevant peptide-treated T2 cells. By performing a peptide dose titration analysis (as described by Zeh, H. J., et al., *Hum. Immunol.* 39:79 (1994), the disclosure of which is incorporated herein by reference), a qualitative assessment of the relative binding capacity of each peptide for HLA-A2 was obtained. The results shown in FIG. 11 show that the Flu M1 58–66 (■) and p53 274–282 peptides (□) were quite effective in stabilizing HLA-A2 expression on the T2 cell line (half-maximal activity at ~5 nM), while the p939 peptide (▲) was less effective (half-maximal activity at ~200 nM). The efficacy of the p939 peptide was comparable to that observed for the gp100 280–288 peptide (○) which was recenlty identified by Cox, A. L., et al., *Science (Wash. DC)* 264:716 (1994), the disclosure of which is incorporated herein by reference, as a melanoma-associated, HLA-A2-presented T cell epitope. The gp100 280–288 peptide was similarly reported by Cox, A. L., et al., to bind HLA-A2 with intermediate-to-low affinity. As controls, the p53 186–196 (□) stabilized HLA-A2 very poorly and the HLA-A3 binding HIV-nef 73–82 peptide (●) did not stabilize HLA-A2, as previously reported by Zeh, H. J., et al., *Hum. Immunol.* 39:79 (1994).

A T cell epitope was generated by pulsing HLA-2⁺ cells with p939 in the following example.

EXAMPLE 18

Epitope reconstitution experiments using peptide p939 (SEQ ID NO: 38) were performed as described above in the section on reconstitution of T cell epitopes. Sensitization of T2 cells to lysis by antimelanoma CTL was evaluated over a wide range of peptide concentrations (250 nM-2.5 pM) as shown in FIGS. 12A–12D. Four different HLA-A2 restricted, antimelanoma CTL were evaluated in these studies: the bulk cultured TIL 1235 line (FIG. 12A), two CTL clones (A83 and A42) (FIGS. 12B and 12C, respectively), and the fresh TIL 6970 line. These melanoma-specific CTL were assayed in 4 hours cytotoxicity assays as described above at effector-to-target ratios of 10:1 against $^{51}$Cr-labeled T2 cells that were pulsed with p939 at the indicated concentrations. The lysis of T2 cells not pulsed with p939 was <5%.

Despite the apparent low affinity of p939 for HLA-A2, each of these four CTL recognized peptide-pulsed T2 targets. Interestingly, while half-maximal sensitization for lysis mediated by TIL 1235, clone A83, and TIL 6970 were reached at approximately 10 pM of peptide, the A42-clone required approximately 3,000 pM of peptide for half-maximal sensitization. TIL 1235 and CTL clone A42 recognition of p939-pulsed T2 targets also resulted in peptide-specific release of interferon-γ at p939 doses as low as 1 pM (data not shown). An additional HLA-A2-restricted fresh melanoma TIL 5403 was also able to recognize and lyse T2 cells pulsed with p939 peptide (data not shown). Evidence to support the presentation of p939 by HLA-2 was documented by the ability of the anti-HLA-A2 monoclonal antibody CR11-351 to inhibit cytolysis of T2 cells pulsed with p939 (data not shown).

As shown by the foregoing, the methods of the present invention have yielded identification of a naturally processed, melanoma-associated T cell epitope that is recognized by five distinct HLA-A2-restricted, tumor-specific CTL lines and clones. The p939 epitope is one of three epitopes coordinately recognized by two distinct antimelanoma CTL clones, A83 and A42 (derived from two different HLA-A2⁺ patients).

One of the aspects of the present invention as demonstrated by the forgoing is that p939 identified herein possesses low affinity for HLA-2 and therefore appears to have more stringent requirements for presentation to T cells. As shown above in Example 18, epitope reconstitution was carried out in the presence of exogenous human $\beta_2$-m and MA2.1 (anti-HLA-A2 monoclonal antibody). These additions generally have been found to enhance peptide loading of various peptides into HLA-A2 complexes by 100–1000 fold. See, generally, Wolfel, T., et al., *Eur. J. Immunol.* 24:759 (1994), Zeh, H. J., et al., *Hum. Immunol.* 39:79 (1994), Boyd, L. F., et al., *Proc. Natl. Acad. Sci. USA* 89:2242 (1992), and Bodmer, H., et al., *Nature (Lond.)* 342:443 (1989), the disclosures of which are incorporated herein by reference. Without these additions, there is only marginal CTL reactivity (5–10% over background) against p939-loaded T2 target cells. This requirement for $\beta_2$-m and MA2.1 appears to reflect the apparent low affinity of p939 for HLA-A2 in the assay system of the present invention. Currently this enhancement function appears to be unique to the MA2.1 antibody, but it is likely that other antibodies will have similar properties and will be within the scope of the present invention.

Despite this low affinity, enough p939 peptide was presented in HLA-A2 complexes on the cell surface of Mel 9742 cells to allow for CTL reactivity as well as to allow for p939 identification. p939 peptide appears to be efficiently processed and loaded into HLA-A2 molecules via the endogenous pathway in melanoma cells. p939 derived according to the present invention may therefore serve as an effective immunogen for cancer patients as a component of a peptide-based vaccine.

It is clear from the forgoing that T cell epitopes identified by the present invention can be produced synthetically and used to produce peptide vaccines (peptide alone, or any agent incorporating the peptide). For example, synthetic viral peptides may be coupled to engineered bacterial lipoproteins with the lipoproteins serving to prime the immune response. Suitable carriers include mycobacterial-containing adjuvants, BCG, and cytokines such as IL-2–IL-12, interferons, and tumor necrosis factor. Alternatively, DNA sequences encoding relevant T cell epitopes and resulting in the expression of these T cell epitopes in transfected cells may be administered to patients as a form of gene therapy. It is to be noted that peptides derived by the present invention, and in particular those having low affinities for HLA and which have special loading requirements such as p939 described herein may best be incorporated into patient therapies in the form of ex vivo pulsed autologous antigen presenting cells (i.e., dendritic cells) or moderate-to-high dose intradermal immunization in addition to use as a vaccine. Alternatively, T cell epitopes derived according to the present invention such as p939 may be used to expand antimelanoma CTL in vitro for subsequent adoptive immunotherapy.

Although the invention has been described in detail for the purpose of illustration, it is to be understood that such detail is solely for that purpose and that variations can be made therein by those skilled in the art without departing from the spirit and scope of the invention except as it may be limited by the claims.

We claim:

1. A pharmaceutical composition, comprising:

T cell epitopes consisting of peptides which have been presented by major histocompatibility complex ("MHC") molecules expressed on the cell surface of viable cells and which do not need further processing for subsequent presentation by MHC molecules to allow for T cell immune recognition, obtained by eluting said T cell epitopes from said cells, said method comprising the steps of:

incubating said cells in the presence of peptide elution buffer such that said cells remain viable; and recovering said T cell epitopes from said peptide elution buffer.

2. The pharmaceutical composition of claim 1, wherein said T cell epitopes are selected from the group consisting of fractions P1, P2 and P4 fractionated on an HPLC linear gradient of from 0% acetonitrile/99.92% water/0.08% trifluoroacetic acid to 35% acetonitrile/64.93% water/0.07% trifluoroacetic acid such that P1 elutes at an acetonitrile concentration of about 19–21.5% acetonitrile; P2 elutes at an acetonitrile concentration of about 21.5–23.5% acetonitrile; and P4 elutes at an acetonitrile concentration of about 25–25.5% acetonitrile.

3. The pharmaceutical composition of claim 1, wherein said T cell epitopes are selected from the group consisting of fractions P1–P6 fractionated on an HPLC linear gradient from 0% acetonitrile/99.92% water/0.08% trifluoroaoacetic acid to 35% acetonitrile/64.93% water/0.07% trifluoroacetic acid such that P1 elutes at an acetonitrile concentration of about 19–21.5% acetonitrile; P2 elutes at an acetonitrile concentration of about 21.5–23.5% acetonitrile; P3 elutes at an acetonitrile concentration of about 23.5–24.5% acetonitrile; P4 elutes at an acetonitrile concentration of about 25–25.5% acetonitrile; P5 elutes at an acetonitrile concentration of about 25.5–26.5% acetonitrile; and P6 elutes at an acetonitrile concentration of about 26.5–28.5% acetonitrile.

4. The pharmaceutical composition of claim 3, wherein said T cell epitopes are selected from the group consisting of peaks 1, 2, and 3 obtained from HLA-A2+ melanoma cells wherein said peaks are shown in FIGS. 9A–9C.

5. The pharmaceutical composition of claim 4, wherein said melanoma cells are selected from the group consisting of Mel 9742 and Mel 624.

6. The pharmaceutical composition of claim 5 wherein said T cell epitope consists of a synthetic peptide having the sequence identified for the peptide p939 (SEQ ID NO: 38).

7. A T cell epitome consisting of T cell epitope p939 (SEQ ID NO: 38), wherein said T cell epitope is presented by HLA-2 molecules and recognized by cytotoxic T lymphocytes.

* * * * *